United States Patent [19]
Kubota et al.

[11] Patent Number: 5,154,723
[45] Date of Patent: Oct. 13, 1992

[54] CEREBRAL SURGERY APPARATUS

[75] Inventors: Tetsumaru Kubota; Hitoshi Karasawa; Yuichi Ikeda, all of Tokyo; Toshihiko Hashiguchi, Sagamihara, all of Japan

[73] Assignee: Olympus Optical Co., Ltd., Tokyo, Japan

[21] Appl. No.: 823,629

[22] Filed: Jan. 21, 1992

Related U.S. Application Data

[63] Continuation of Ser. No. 511,809, Apr. 17, 1990, abandoned, which is a continuation of Ser. No. 136,782, Dec. 21, 1981, abandoned.

[30] Foreign Application Priority Data

| Dec. 2, 1987 | [JP] | Japan | 62-305431 |
| Dec. 2, 1987 | [JP] | Japan | 62-305432 |
| Dec. 2, 1987 | [JP] | Japan | 62-305433 |
| Dec. 2, 1987 | [JP] | Japan | 62-305434 |

[51] Int. Cl.$^5$ ............................................. A61B 19/00
[52] U.S. Cl. ..................................... 606/130; 128/4; 128/6
[58] Field of Search ............... 606/130; 128/4–6, 128/7–9

[56] References Cited

U.S. PATENT DOCUMENTS

| 3,941,121 | 3/1976 | Olinger et al. | 128/6 |
| 4,386,602 | 6/1983 | Sheldon et al. | 128/4 |

FOREIGN PATENT DOCUMENTS

| 2115121 | 3/1971 | Fed. Rep. of Germany |
| 25377 | 7/1985 | Japan |
| 26088 | 6/1986 | Japan |

Primary Examiner—C. Fred Rosenbaum
Assistant Examiner—William W. Lewis
Attorney, Agent, or Firm—Armstrong & Kubovcik

[57] ABSTRACT

A cerebral surgery endoscope apparatus comprises a stereotaxic instrument secured to the head of a patient and adapted to effect positioning of an affected part; an adjusted support means whose inserting direction is determined by its orientation to the stereotaxic instrument and which determines the direction in which a treating instrument is inserted into the head of the patient; a viewing device such as an endoscope supported on the support means and having a channel into which a treating instrument can be inserted, the treating instrument being inserted into a channel of the viewing device and then into the head of the patient. A fixing device is connected to the stereotaxic instrument and adapted to secure the support means, the viewing device and/or the treating instrument in a fixed position on with respect to the affected part.

45 Claims, 29 Drawing Sheets

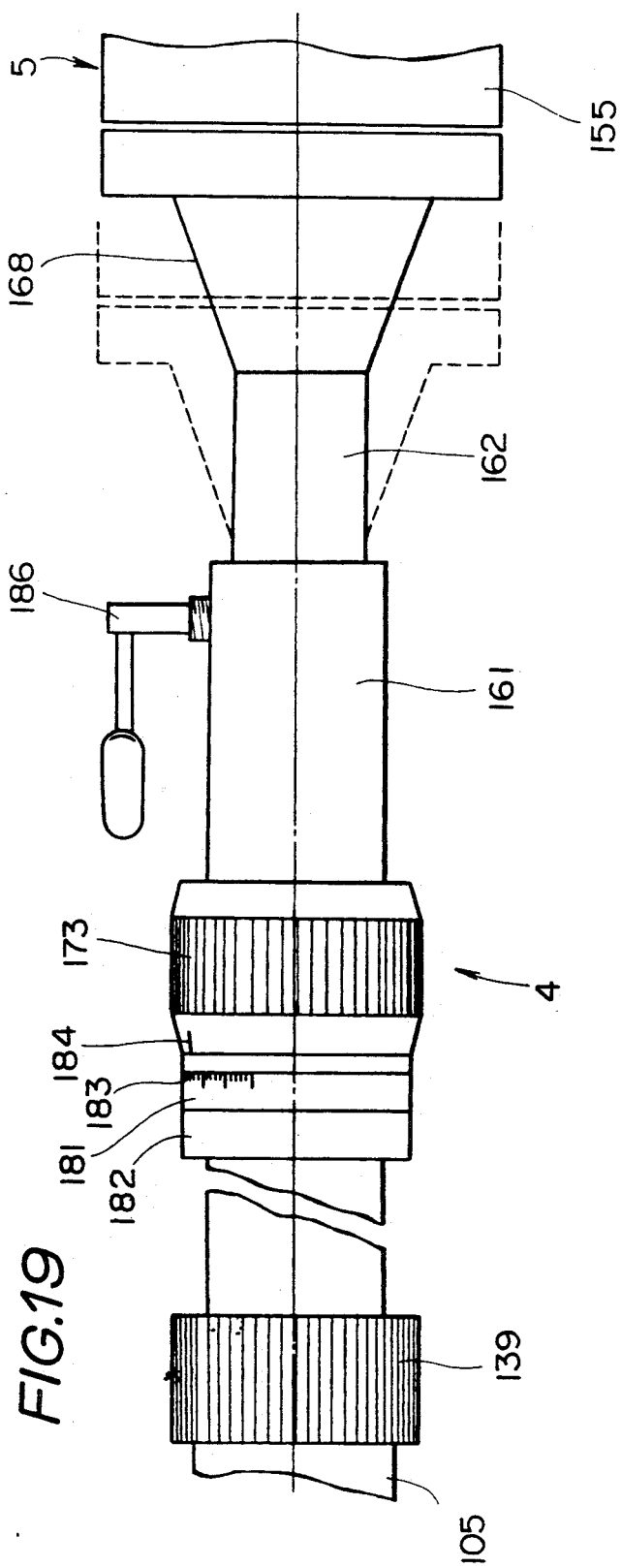
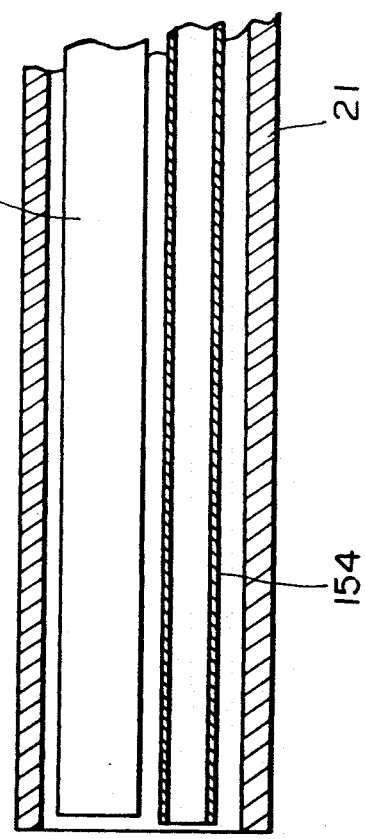

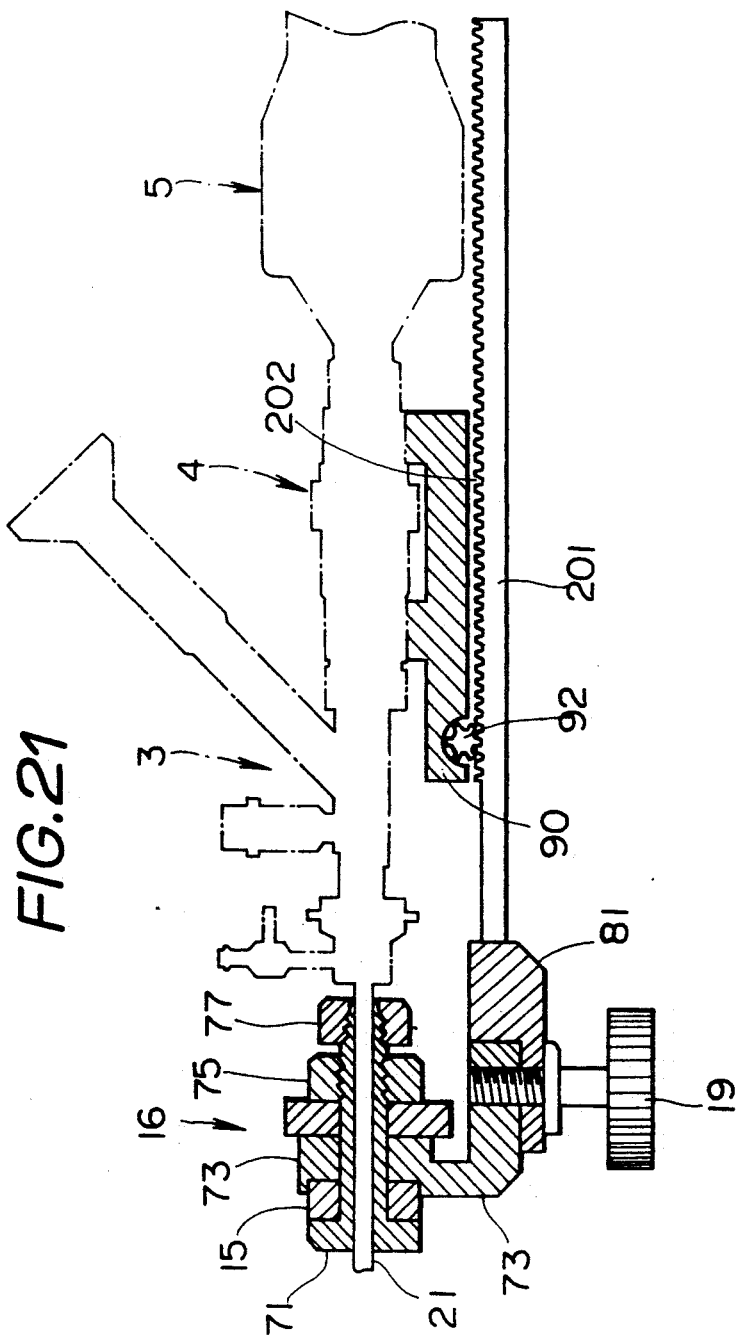

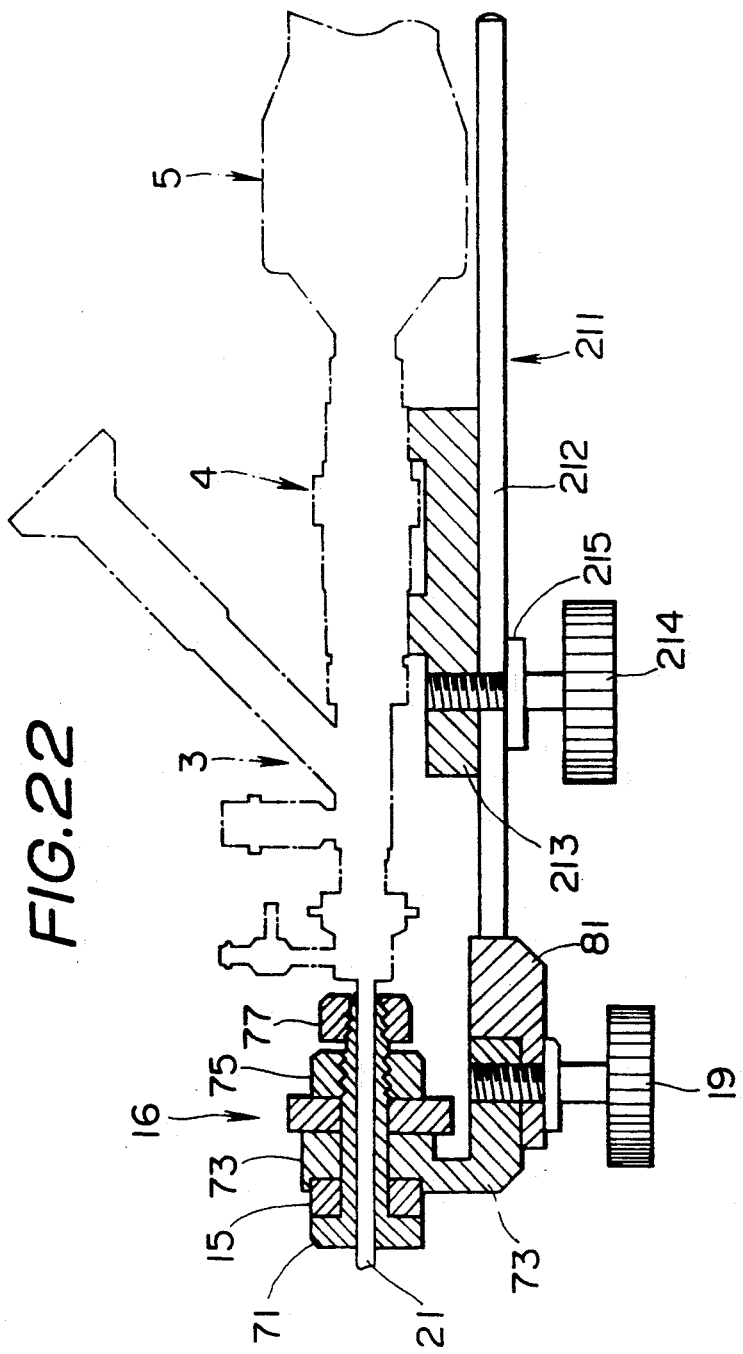

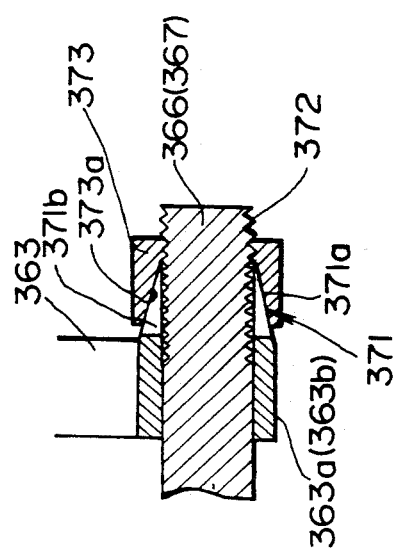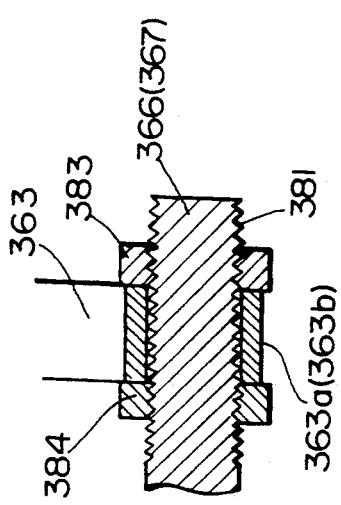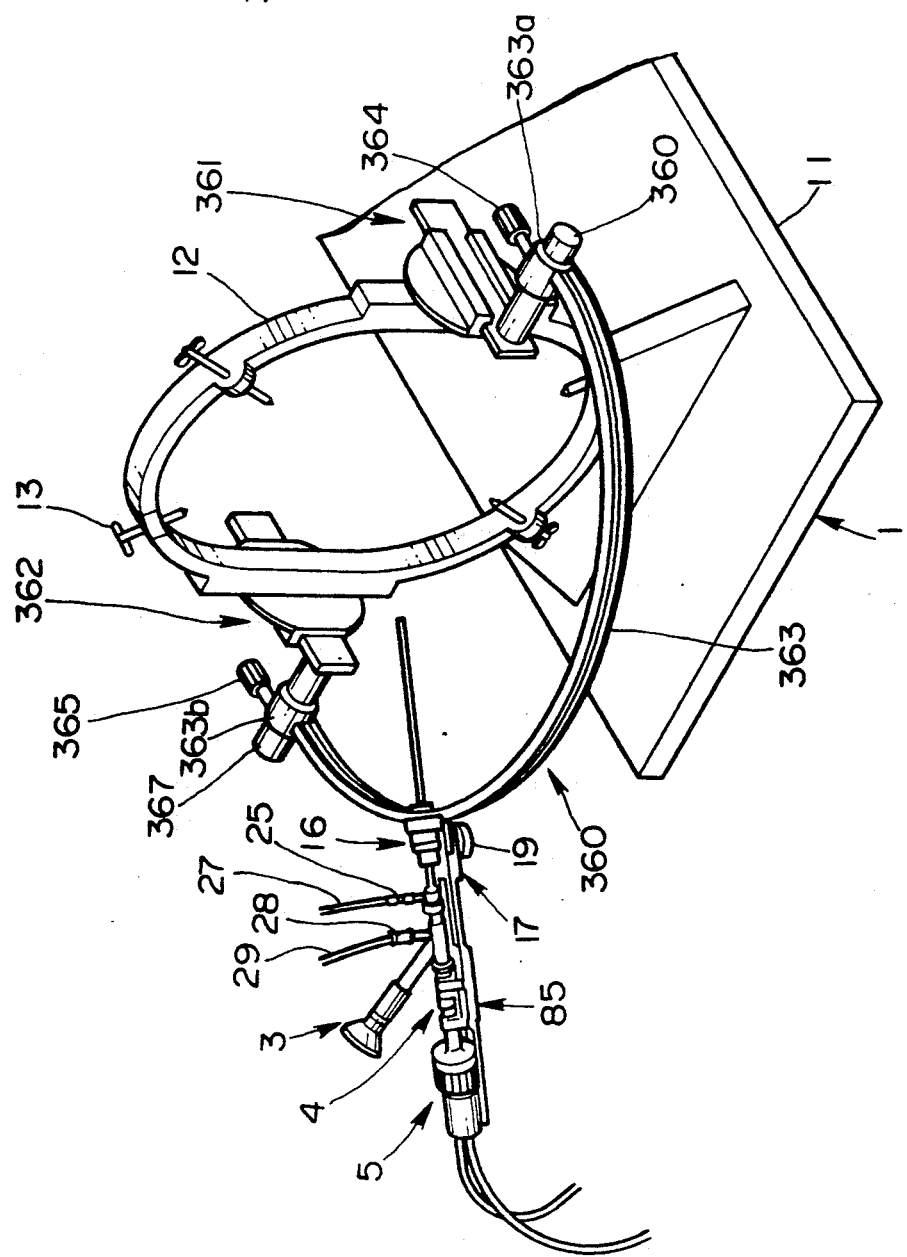

CEREBRAL SURGERY APPARATUS

This application is a continuation of application Ser. No. 511,809 filed Apr. 17, 1990 which is a continuation of application Ser. No. 136,782 filed on Dec. 21, 1987, now both abandoned.

BACKGROUND OF THE INVENTION

1. Field of the Invention

The present invention relates to an apparatus used in a surgical operation in cranial bones, and, more particularly, to a cerebral surgery apparatus for sucking and removing an affected part such as an intracerebral hematoma, a cerebral tumor, or the like.

2. Related Art Statement

Cerebral hemorrhage and subarachnoid hemorrhage can be cited as typical examples of cerebrovascular diseases. In recent years, stereotaxy using a CT (computer tomography) drainage method is conducted to remove an intracerebral hematoma or the like after the occurrence of an intracerebral hemorrhage, as shown in the "Journal of Brain Neurosurgery", Vol. 14, No. 2, pp. 123-133, published in February 1986.

In stereotaxy, a stereotaxic instrument is fixed to the head of a patient and is positioned in relation to an affected part in the brain by using a positioner provided in the instrument, and a treating instrument, such as a drainage tube, is inserted into the affected part, thereby allowing surgery to be conducted. In this type of stereotaxic surgery, the positioning accuracy has in recent years been improved by the use of CT in which an affected part is determined on the basis of a cross-sectional image of CT to allow positioning to be effected. Consequently, it has become possible to check at a microscopic level the intervention to which the patient is subjected.

Examples of surgical apparatuses that are used in this type of stereotaxy are disclosed in Japanese Patent Publication No. 25377/1986, Japanese Utility Model Publication No. 26088/1987, etc.

As a method of removing an intracerebral hematoma by stereotaxy, it is conventional for a method to be adopted in which a metal suction tube is inserted into the hematoma, and the hematoma is sucked and removed by a suction instrument such as a syringe. If the hematoma cannot be removed completely, a method is adopted in which an indwelling tube is left in a hematoma hole, a hematoma-resolving agent such as urokinase is injected, and the resolved hematoma is sucked and removed from the indwelling tube several hours later.

Another method has also come to be adopted in which a hematoma is broken down, sucked and removed by using an ultrasonic suction device.

Furthermore, biopsy of cerebral tumors, thermocautery, or the like using, for instance, Nd-YAG laser beams, is conducted by stereotaxy.

In the removal of a stereotaxic intracerebral hematoma using the CT drainage method, the state of suction of a hematoma cannot be observed on a real-time basis, so that a surgical operation is performed in a blind manner. Consequently, there is the risk of causing damage to a cerebral parenchyma. In addition, there are also cases where the intracerebral hematoma cannot be removed completely when undue efforts are made not to damage the cerebral parenchyma. Furthermore, since it is essential to proceed with the surgical operation while successively confirming the state in which the hematoma is being sucked so as not to cause damage to the cerebral parenchyma, the time of an operation tends to become extremely long. This means that the patient is subjected to a large scale invasion and the operator inevitably experiences considerable strain and fatigue.

In addition, the method of sucking and removing a hematoma by means of a sucking device such as a syringe involves problems in that the sucking pressure must be increased to a substantially high level due to the highly viscose nature of the hematoma, with the attendant danger of sucking the cerebral parenchyma as well due to the high sucking pressure, and in that the hematoma is liable to become clogged in the inner hole of the suction tube which can frequently cause the operation to be interrupted.

The diameter of the suction tube must be enlarged in order to render clogging with a hematoma less likely to occur, so that the degree of damage caused in the cerebral parenchyma increases by that margin.

In addition, in the hematoma resolving method, the resolution power of the hematoma resolvent is very small, and the situation is not such that this method can ever be clinically satisfactory. Hence, because of the retention of a catheter for a long period of time and the frequent administration of a resolvent, the possibility of a concurrent infectious disease is unavoidable, and the agony experienced by the patient is very great due to the retention of the catheter over a long period of time.

Furthermore, although the method that utilizes an ultrasonic suction device is very effective, there is a risk of causing damage to the cerebral parenchyma owing to the fact that the operation is conducted blind. In addition, since no device is available for fixing the ultrasonic suction device that would be capable of effecting an advancing and retracting operation, the advancing and retracting operation must be performed manually with the apparatus held by the operator's hand. Consequently, there is a danger that damage of the cerebral parenchyma will be caused inadvertently.

The above-mentioned drawbacks are not confined to the suction and removal of intracerebral hematomas, but are also commonly experienced in conventional stereotaxy, including operations on cerebral tumors.

SUMMARY OF THE INVENTION:

Accordingly, an object of the present invention is to provide a cerebral surgery endoscope apparatus which is capable of performing treatment of an affected part, such as a hematoma and a tumor, safely and positively within a short period of time, while orthoptically observing the state of treatment of the affected part on a real-time basis.

Another object of the present invention is to provide a cerebral surgery endoscope apparatus which is capable of accurately effecting the positioning of a surgical instrument and of positively holding and fixing the surgical instrument.

Still another object of the present invention is to provide a cerebral surgery endoscope apparatus which is capable of positively effecting the positioning and holding of a surgical instrument and of accurately and positively adjusting the position of the surgical instrument relative to the head of a patient.

A further object of the present invention is to provide a cerebral surgery endoscope apparatus which is capable of performing an advancing and retracting operation of a treating instrument, as desired, and is capable of fixing the same at a desired position.

To these ends, in accordance with the present invention, there is provided a cerebral surgery endoscope apparatus comprising: a stereotaxic instrument secured to the head of a patient and adapted to effect positioning of a treating instrument in an affected part; a sheath or treating instrument inserting means whose inserting direction is determined by the stereotaxic instrument and which is inserted into the head; a telescope or other viewing instrument detachably inserted into the sheath and having a channel into which a treating instrument can be treating the inserting instrument being adapted to be inserted into a channel of the telescope and then into the head of the patient; an adapter for detachably connecting the treating instrument and the telescope; and a fixing device connected to the stereotaxic instrument and adapted to support and fix the sheath, the telescope, the adapter, and the treating instrument.

Other objects, features and advantages of the present invention will become apparent from the following detailed description of the invention when read in conjunction with the accompanying drawings.

BRIEF DESCRIPTION OF THE DRAWINGS

FIGS. 1 to 20 relate to a first embodiment of the present invention, in which

FIG. 1 is a perspective view illustrating an overall cerebral surgery apparatus;

FIG. 2 is a side-elevational view of a state in which a sheath, a telescope, an adapter, an ultrasonic suction instrument, and a fixing device are assembled;

FIG. 3 is a cross-sectional view of the sheath;

FIG. 4 is a side-elevational view of a mandrel;

FIG. 5 is a perspective view of the fixing device;

FIG. 6 is a cross-sectional view illustrating a mechanism for adjusting the fixing device;

FIG. 7 is a cross-sectional view taken along the line B—B' of FIG. 6;

FIG. 8 is a side-elevational view of a sheath holder;

FIG. 9 is a cross-sectional view taken along the line C—C' of FIG. 8;

FIG. 10 is a cross-sectional view illustrating a connecting portion for connecting the sheath holder and a support;

FIG. 11 is a cross-sectional view of the telescope;

FIG. 12 is a front-elevational view of a tip portion of an inserting portion of the telescope;

FIG. 13 is a cross-sectional view taken along the line D—D' of FIG. 12;

FIG. 14 is a cross-sectional view illustrating a slider of the support;

FIG. 15 is a cross-sectional view taken along the line E—E' of FIG. 14;

FIG. 16 is a cross-sectional view taken along the line A—A' of FIG. 2 and illustrating a fixing portion for fixing the slider and an adapter;

FIG. 17 is a cross-sectional view of the adapter;

FIG. 18 is a cross-sectional view illustrating the positional relationship between a probe and a sheath-inserting portion with a sliding member of the adapter disposed at its forward limit;

FIG. 19 is a side-elevational view of the adapter;

FIG. 20 is a cross-sectional view illustrating the positional relationship bettween the probe and the sheath-inserting portion with the sliding member of the adapter disposed at its rearward limit;

FIG. 21 is a cross-sectional view illustrating the slider of the support in accordance with a second embodiment of the present invention;

FIG. 22 is a cross-sectional view illustrating the slider of the support in accordance with a third embodiment of the present invention;

FIGS. 23 and 24 relate to a fourth embodiment of the present invention; in which FIG. 23 is a cross-sectional view of the adapter;

FIG. 24 is a cross-sectional view of a cross-sectional view taken along the line F—F' of FIG. 23;

FIGS. 33 and 34 relate to a thirteenth embodiment of the present invention; in which FIG. 33 is a perspective view illustrating the overall cerebral surgery apparatus;

FIG. 34 is a cross-sectional view illustrating a connecting portion for connecting a tube and the support of the fixing device ;

FIG. 35 is a perspective view illustrating the overall cerebral surgery apparatus;

FIG. 36 is a top plan view illustrating a stage of the fixing device;

FIGS. 38 to 41 relate to a sixteenth embodiment of the present invention, in which FIG. 38 is a perspective view illustrating the overall cerebral surgery apparatus;

FIG. 39 is a cross-sectional view of an example of a fixing portion of an arm of a stereotaxic apparatus;

FIG. 40 is a cross-sectional view illustrating another example of the fixing portion of the arm of the stereotaxic apparatus; and FIG. 41 is a perspective view illustrating the cerebral surgery apparatus with an inner ring installed in a ring of the stereotaxic apparatus.

DESCRIPTION OF THE PREFERRED EMBODIMENTS

FIGS. 1 to 20 illustrate a first embodiment of the present invention.

Figure 1:
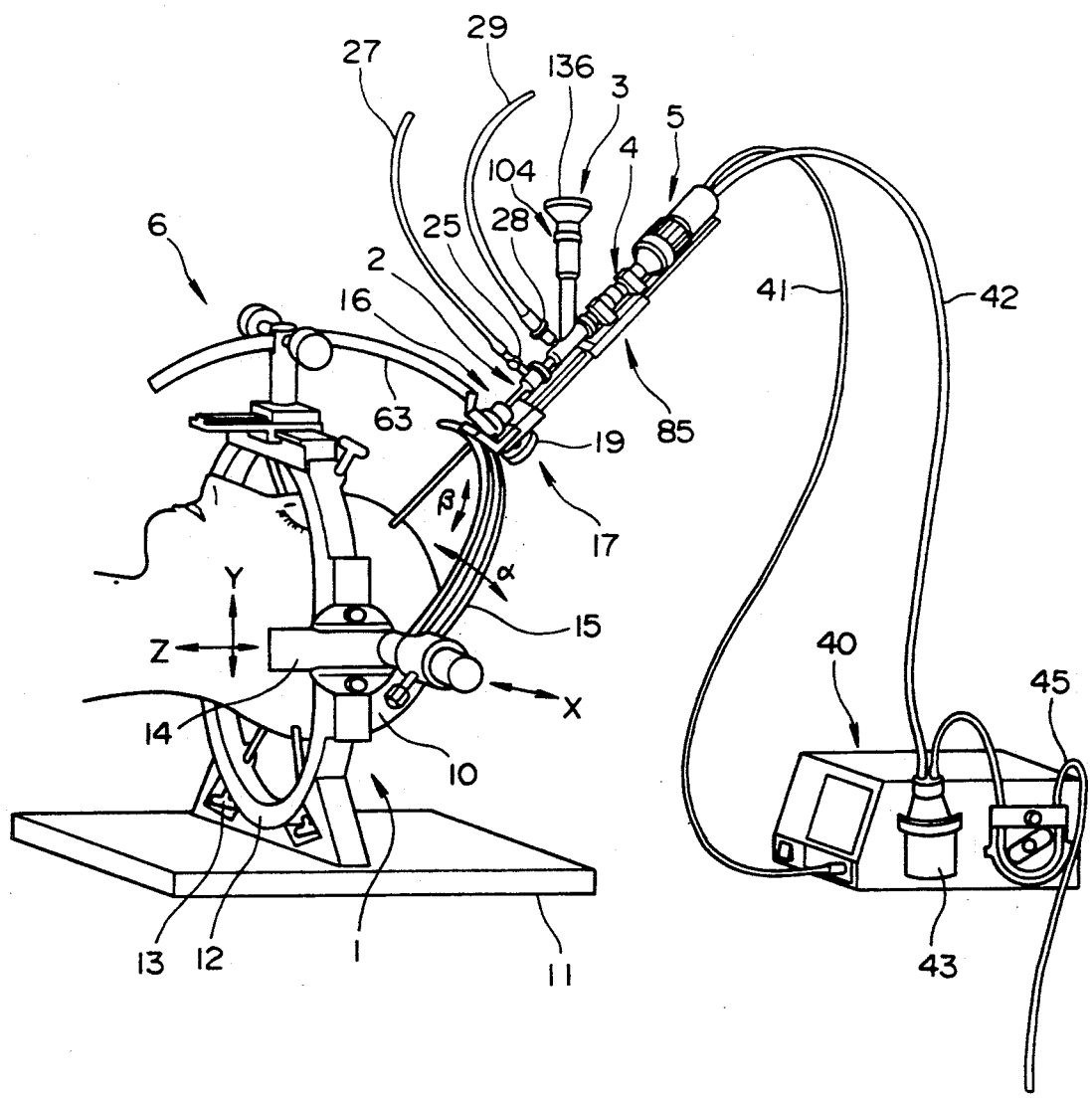

As shown in FIG. 1, a cerebral surgery apparatus in accordance with this embodiment comprises: a stereotaxic instrument 1 which is fixed to the head of a patient and adapted to effect the positioning of an affected part; a sheath or treating instrument inserting means 2 whose inserting direction is determined by this stereotaxic instrument and which is inserted into the affected part; a telescope 3 which is detachably inserted into this sheath 2; an ultrasonic suction device 5 which is a treating instrument inserted retractably into a treatment instrument channel of the telescope 3; an adapter 4 which detachably connects the ultrasonic suction device 5 and the telescope 3; and a fixing device 6 which is connected to the sterotaxic instrument 1 and integrally supports the sheath 2, the telescope 3, the adapter 4, and the ultrasonic suction device 5.

The stereotaxic instrument 1 has a ring 12 secured on an operating table 11, and the head 10 of the patient is inserted into the ring 12 and is adapted to be secured to the stereotaxic instrument 1 by means of, say, four head-securing screws 13 disposed on the ring 12. An arm 15 is connected via a positioner 14 to one side portion of the ring 12. A sheath holder 16 for holding the sheath 2 is provided on this arm 15. The sheath 2 is adapted to be set at an optimum piercing position when the sheath 2 is adjusted in the X, Y and Z directions by means of the positioner 14 and in the α and β directions by means of the arm 15 and the sheath holder 16 such as to be aligned with the position of the affected part in the brain.

Figure 3:
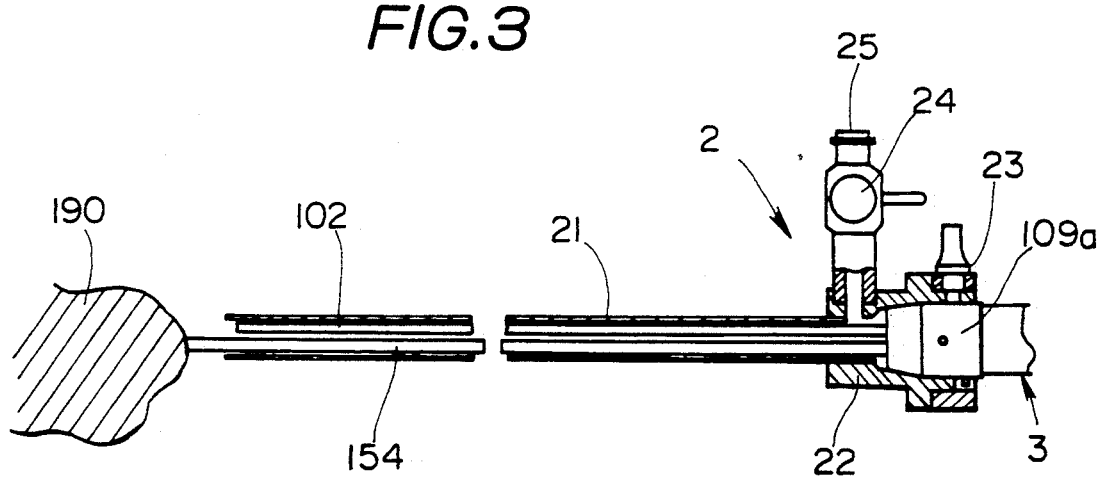

As shown in FIG. 3, the aforementioned sheath 2 has a hollow, elongated sheath-inserting portion 21 and a main body 22 connected to a rear end of the sheath-inserting portion 21. A connecting member 23, to which the telescope 3 or a mandrel 30, which will be described later, can be connected detachably, is provided at a rear end of the main body 22. In addition, a liquid feeding port 25, which communicates with a hollow portion in the sheath-inserting portion 21 and has a cock 24, is provided on a side portion of the main body 22. Incidentally, two liquid feeding ports 25 may be provided to allow both the supply and discharge of the liquid.

Figure 4:
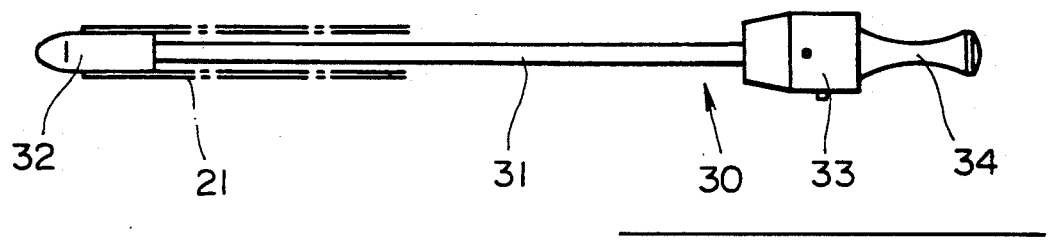

At the time of inserting the sheath 2 into the brain, the sheath 2 is inserted into the brain with the mandrel 30 installed in the sheath 2, as shown in FIG. 4. The mandrel 30 comprises a shaft 31 which is inserted into the sheath-inserting portion 21, a tip portion 32 disposed at a tip of this shaft 31 and having a conical tip, a connecting portion 33 which is connected to a rear end of the shaft 31 and is detachably connectable to the main body 22 of the sheath 2 via a connecting member 23, and a grip 34 connected to a rear end of the connecting portion 33.

The sheath 2 is fixed by the sheath holder 16 disposed on the arm 15. In addition, the positions of the sheath 2 and the sheath holder 16 are fixed by the fixing device 6. As shown in FIG. 1, this fixing device has a support 17 for integrally supporting the sheath 2, the telescope 3, the adapter 4, and the ultrasonic suction device 5. This support 17 and the sheath holder 16 are adapted to be secured by a setscrew 19.

Figure 2:
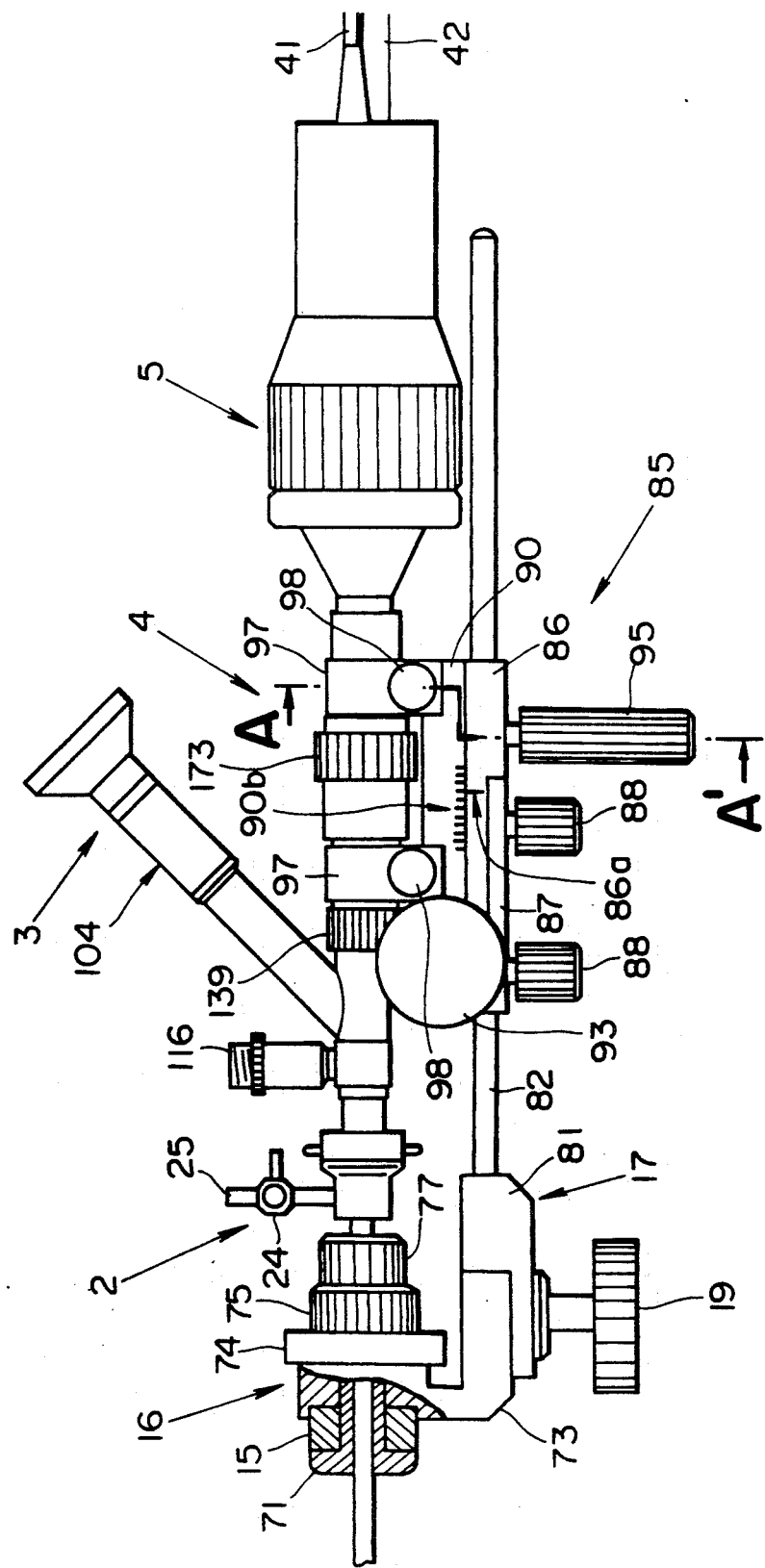

The mandrel 30 is adapted to be withdrawn after the sheath 2 has been inserted into a target point. With the telescope 3, the adapter 4, and the ultrasonic suction device 5 assembled together, as shown in FIG. 2, this assembly, instead of the mandrel 30, is adapted to be inserted into the sheath 2 and connected thereto.

A liquid supply tube 27 which is connected to a liquid feeding device (not shown) is connected to the liquid feeding port 15 of the sheath 2. A light guide 29 which is connected to a light source device (not shown) is connected to a light guide connector 28 of the telescope 3. In addition, an electric cord 41 of the ultrasonic suction device 5 is connected to a generator 40 for driving the ultrasonic suction device 5, and a drainage tube 42 is connected to a collection bottle 43 which is attached to the generator 40 and adapted to collect a discharged liquid. A tube 44 extends from the collection bottle 43, and is connected to a discharged liquid container (not shown) via a pump 45.

The fixing device 6 has an arrangement which is illustrated in FIGS. 5 to 10.

Figure 5:
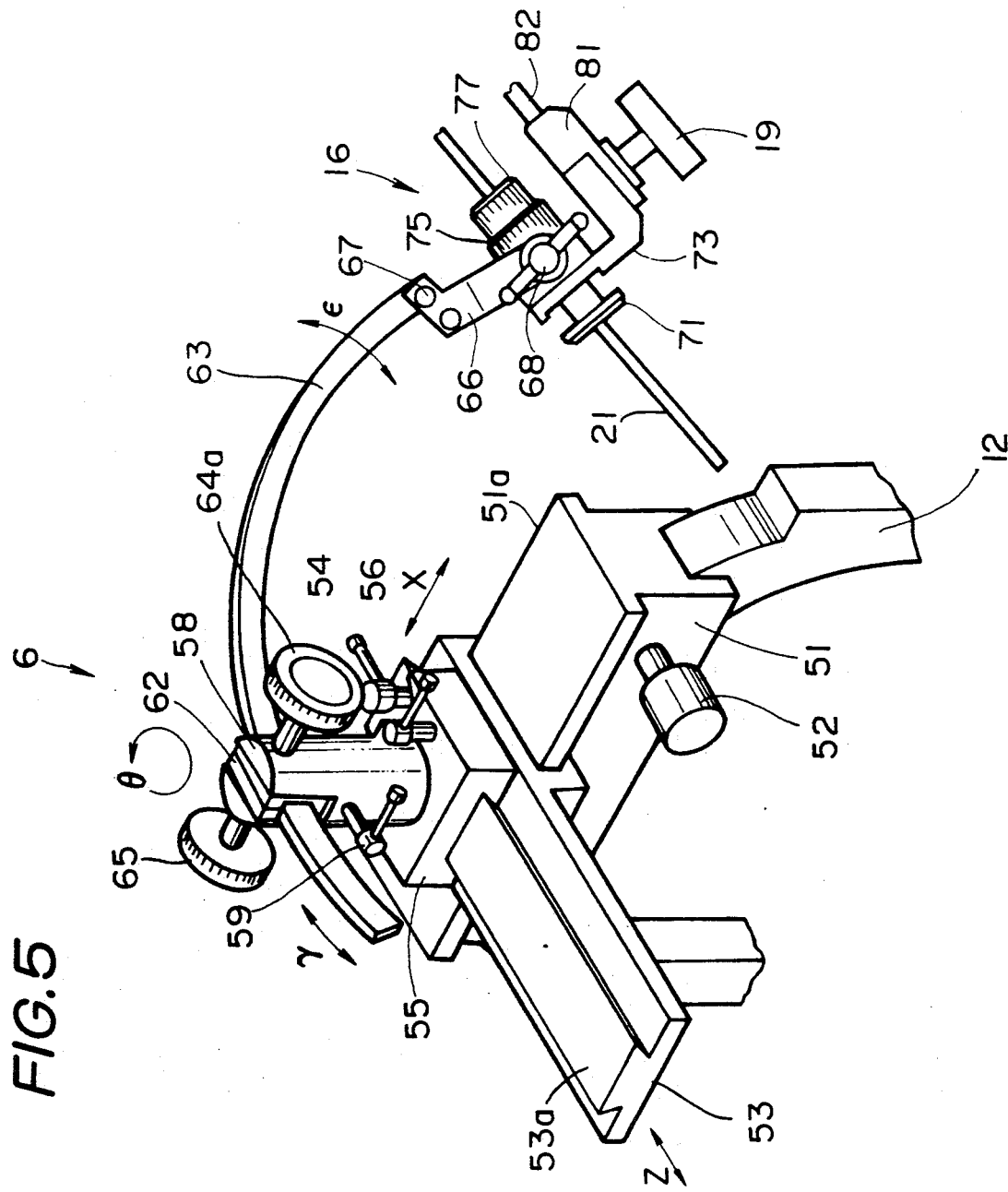

As shown in FIG. 5, a fixing table 51 of the fixing device 6 is disposed on top of the ring 12 of the stereotaxic instrument 1. This fixing table 51 is formed to extend in the direction of X shown in FIG. 5, and is mounted on the ring 12 to be parallel with the operating table 11 of the stereotaxic instrument 1. The fixing table 51 is fixed to the ring 12 by means of a setscrew 52 screwed in from a side portion of the fixing table 51. Flanges 51a are formed on top of the fixing table 51 in the direction of X. A sliding table 53 is installed on the fixing table 51 and is formed to extend in the direction of Z shown in the drawing, to engage with the flanges 51a, and to be slidable in the direction of X. After adjustment of the sliding table 53 in the direction of X is carried out by sliding the same, the sliding table 53 is fixed to the fixing table 51 by a setscrew 54 which is screwed in from a top portion of the fixing table 51. A projection 53a is formed on top of the sliding table 53 along the direction of Z. A support table 55, which engages with the projection 53a and is slidable in the direction of Z, is mounted on the sliding table 53. After adjustment is made of this support table 55 in the direction of Z by sliding the same, this support table 55 is secured to the sliding table 53 by means of a setscrew 56 which is screwed in from the top of the support table 55.

Figures 6, 7:
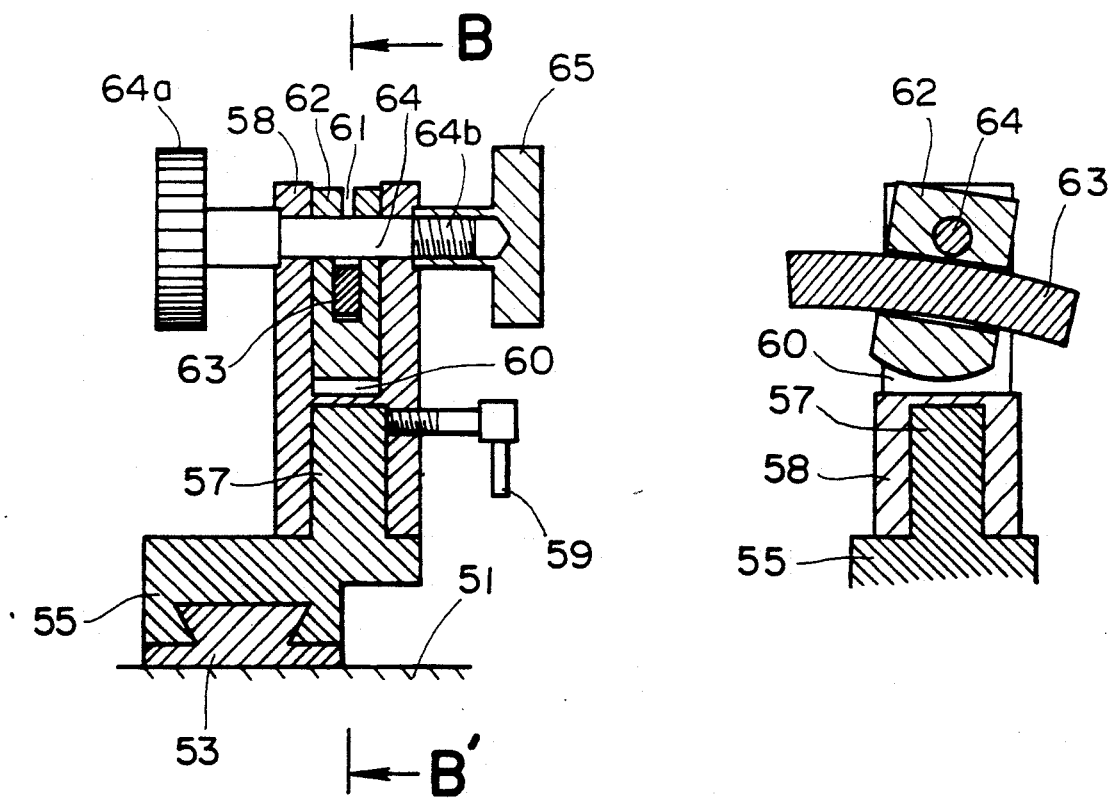

As shown in FIGS. 6 and 7, a cylindrical column 57 projects from the top of the support table 55. A rotational cylinder 58 having a cylindrical hole, into which the column 57 is engaged, is fitted around the lower side of this column 57. This rotational cylinder 58 is rotatable on the column 57, and can be adjusted in the direction of $\theta$ shown in FIG. 5. This rotational cylinder 58 is fixed to the support cylinder 57 by means of a setscrew 59 which is screwed in from a side portion of the rotational cylinder 58. In addition, an upper side of the rotational cylinder 58 is provided with a groove 60, which is open to side surfaces and an upper surface of the rotational cylinder 58. An arm-holding plate 62 provided with a slit 61 is inserted into this groove 60, and an arm 63 is clamped in the slit 61. A shaft 64 having a knob 64a at an end portion thereof penetrates the rotational cylinder 58 and the arm-holding plate 62. An external thread 64b is formed at a tip portion of the shaft 64, on which a knob 65 is screwed onto this external thread 64b. The arm 63 is slidable in the slit 61 in the direction of $\gamma$ shown in FIG. 5. Furthermore, the arm-holding plate 62 is rotatable around the shaft 64, as shown in FIG. 7, thereby making it possible to adjust a rotational angle $\epsilon$ of the arm 63, as shown in FIG. 5. In addition, the arm 63 is arranged to be tightened and fixed by the slit 61 when the rotational cylinder 58 and the arm-holding plate 62 are tightened by the shaft 64 and the knob 65.

Figure 8:
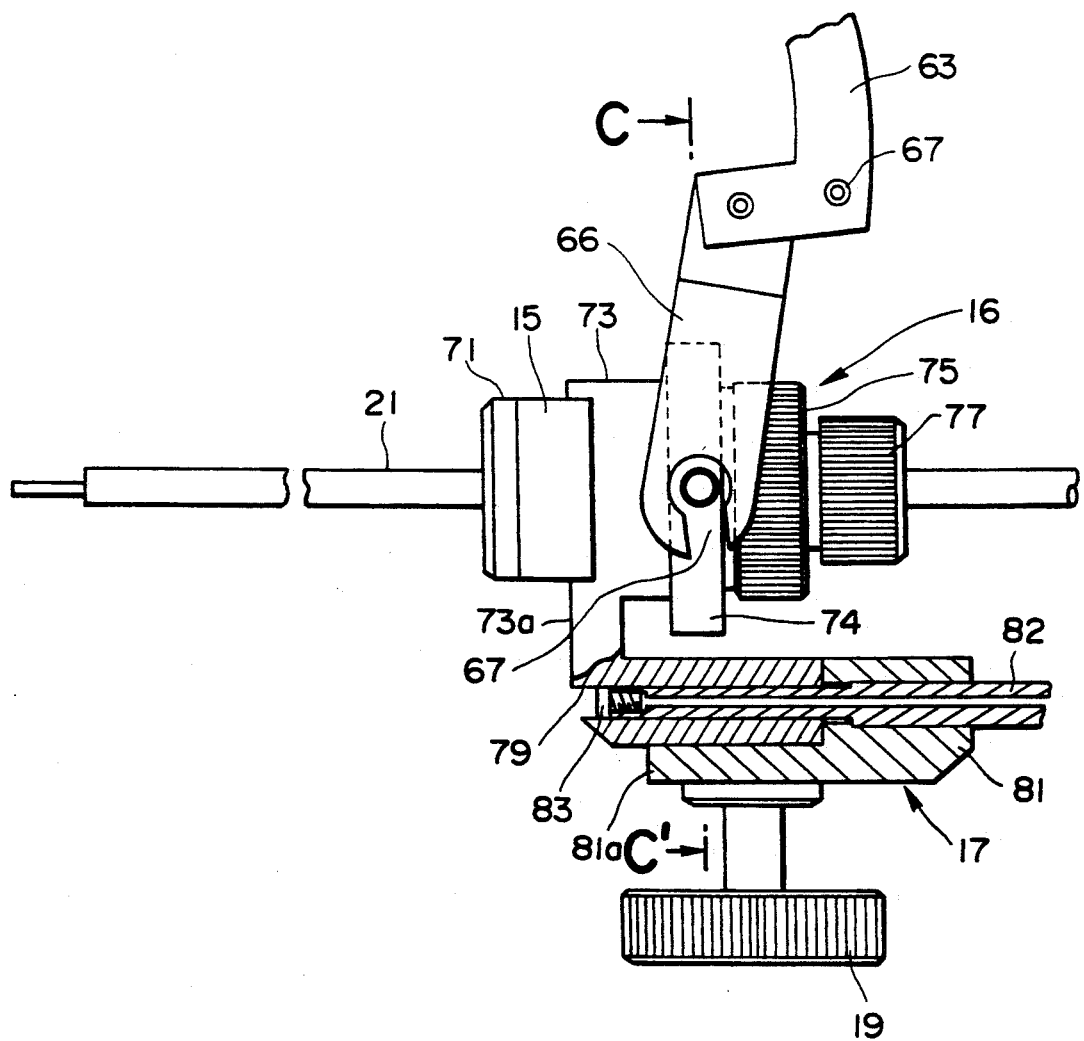
Figure 9:
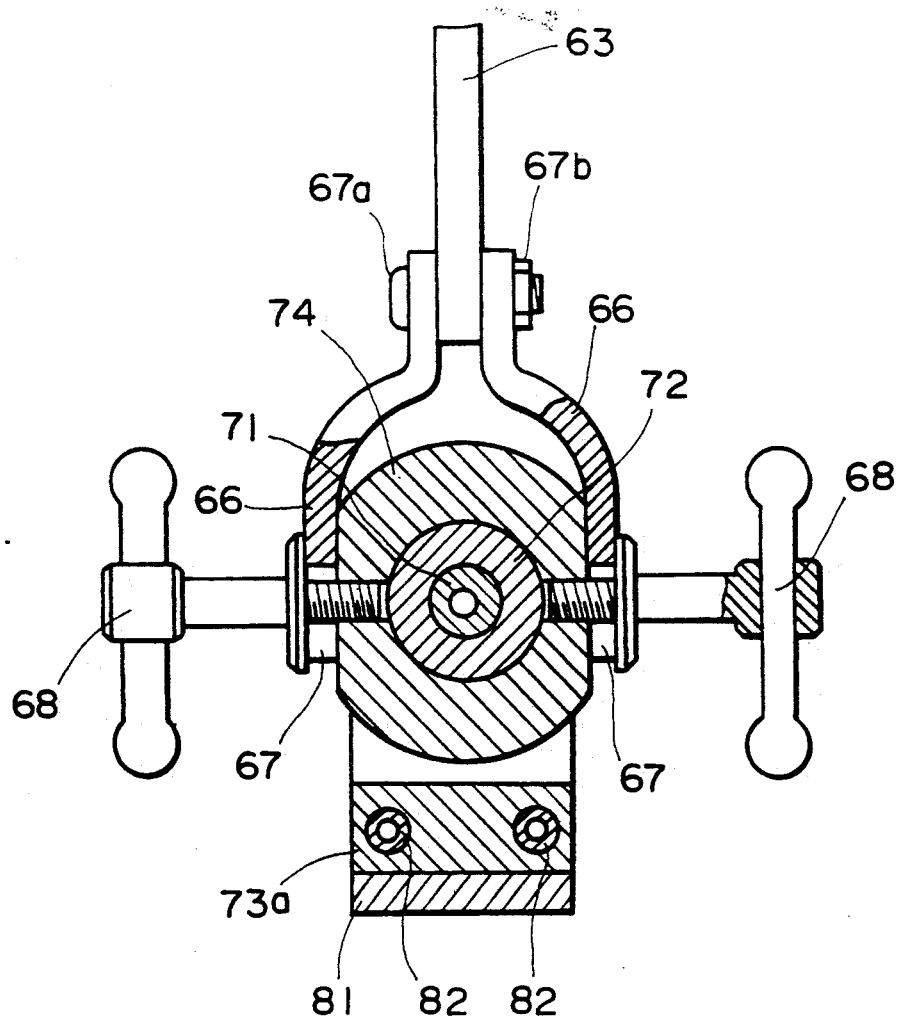

As shown in FIGS. 8 and 9, two auxiliary arms 66 are secured to a tip portion of the arm 63 by means of a bolt 67a and a nut 67b. A rotational member 74 of the sheath holder 16 is clamped between the two auxiliary arms 66, and this rotational member 74 is fixed by setscrews 68 which respectively pass through 67 formed in the auxiliary arms 66 and are screwed into the rotational member 74.

Figure 10:
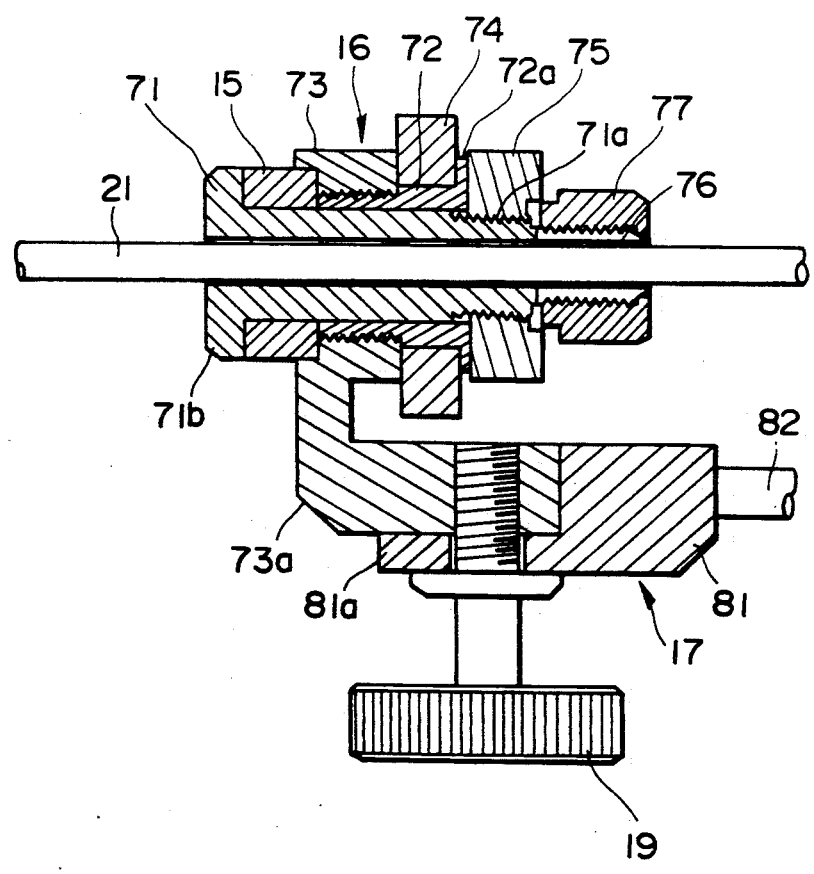

As shown in FIG. 10, the sheath holder 16 has a substantially cylindrical carrier 71 into which the sheath-inserting portion 21 of the sheath 2 is inserted. A holding cylinder 72 is fitted around this carrier 71. A support member 73 is threadingly engaged with an outer peripheral portion of this holding cylinder 72. In addition, the rotational member 74 is fitted around the holding cylinder 72 and is clamped between a flange 72a of the holding cylinder 72 and the support member 73, so as to be rotatable about the holding cylinder 72. Also, the rotational member 74 is clamped between a flange 71b of the carrier 71 and the support member 73. An external thread 71a is formed at a rear-end portion of the carrier 71, and a tightening nut 75 is screwed onto this external thread 71a. The sheath holder 16 is secured to the arm 15 of the stereotaxic instrument 1 when the arm 15 is clamped between the flange 71b formed at a tip of the carrier 71 and the support member 73 and the tightening nut 75 is tightened. A tightening portion 76 is formed at a rear-end portion of the carrier 71. This tightening portion 76 has a tapered surface which is provided with a plurality of slits and an external thread provided on an outer periphery thereof, the smaller diameter of the tapered surface being at its rear end. A nut 77 has a tapered surface which is formed on a rear end portion of an inner peripheral portion thereof and whose small diameter is at its rear end. This nut 77 is screwed onto the tightening portion 76. The sheath-inserting portion 21 can be secured by the tightening portion 76 when the tightening nut 77 is tightened after the sheath-inserting portion 21 has been inserted into the carrier 71.

The support member 73 of the sheath holder 16 has a projection 73a at a lower side thereof, and the support 17 is connected and secured to the projection 73a.

As shown in FIG. 10, the support 17 has a retainer 81, which is secured to the projection 73a of the support member 73 by means of a setscrew 19. Two parallel support shafts 82 extending along the axial direction of the sheath 2 are secured to the retainer 81. As shown in FIG. 8, the distal end side of each of these supports shaft 82 projects from a front end surface of the retainer 81. In addition, a projection 81a projecting forwardly is formed at a bottom portion of the retainer 81. Meanwhile, two holes 79, into which the tip portions of the support shafts 82 are respectively inserted, are formed in the projection 73a of the support member 73. The support shafts 82 are inserted into these holes 79, and the retainer 81 is secured to the support member 73 at a position in which the retainer 81 abuts against the support member 73, by means of the setscrew 19 which is screwed in from the bottom side of the projection 81a of the retainer 81 and penetrates the support member 73 and the retainer 81, as shown in FIG. 10. As shown in FIG. 8, the support shafts 82 are formed such as to be hollow, and caps 83 are fitted at both ends thereof.

Figure 14:
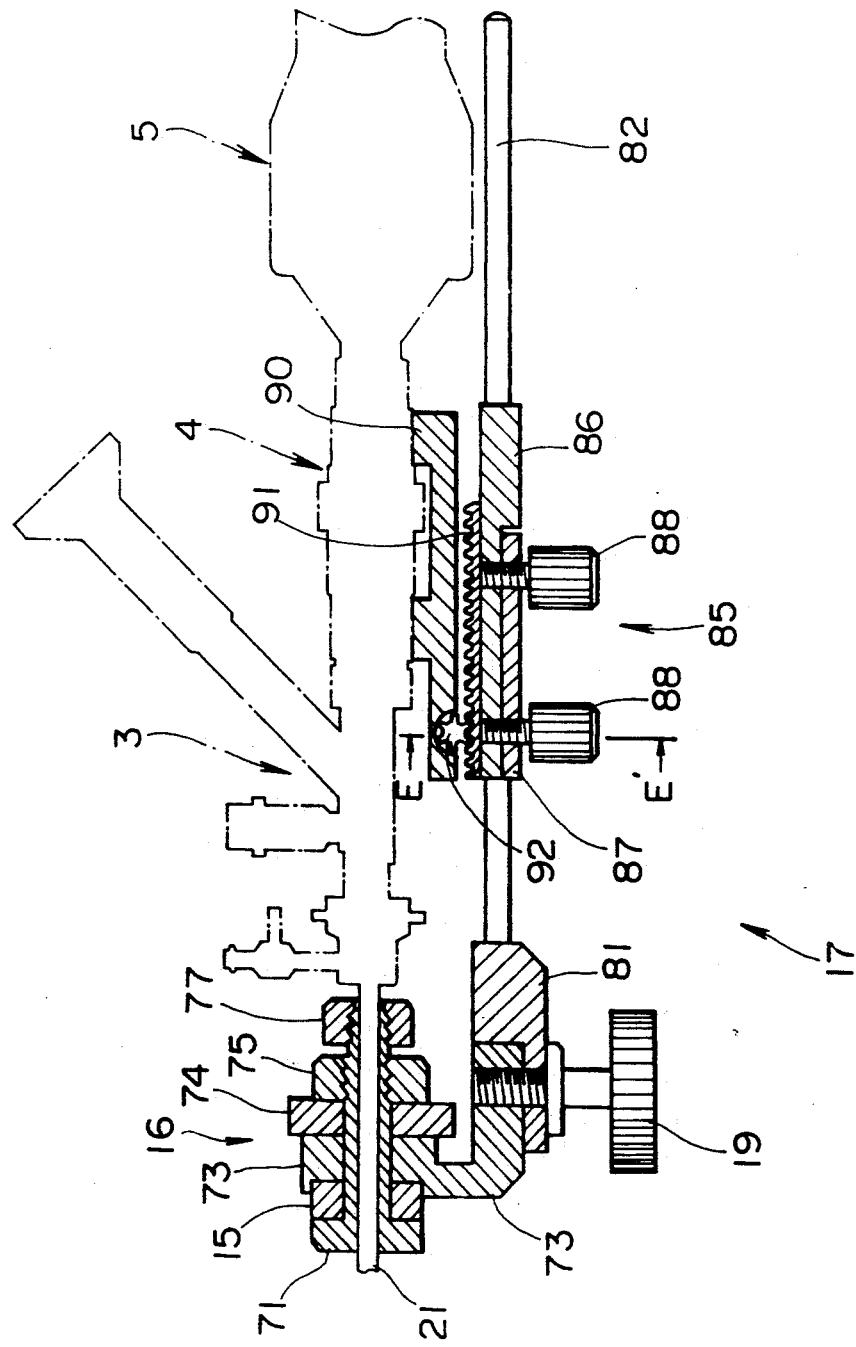
Figure 15:
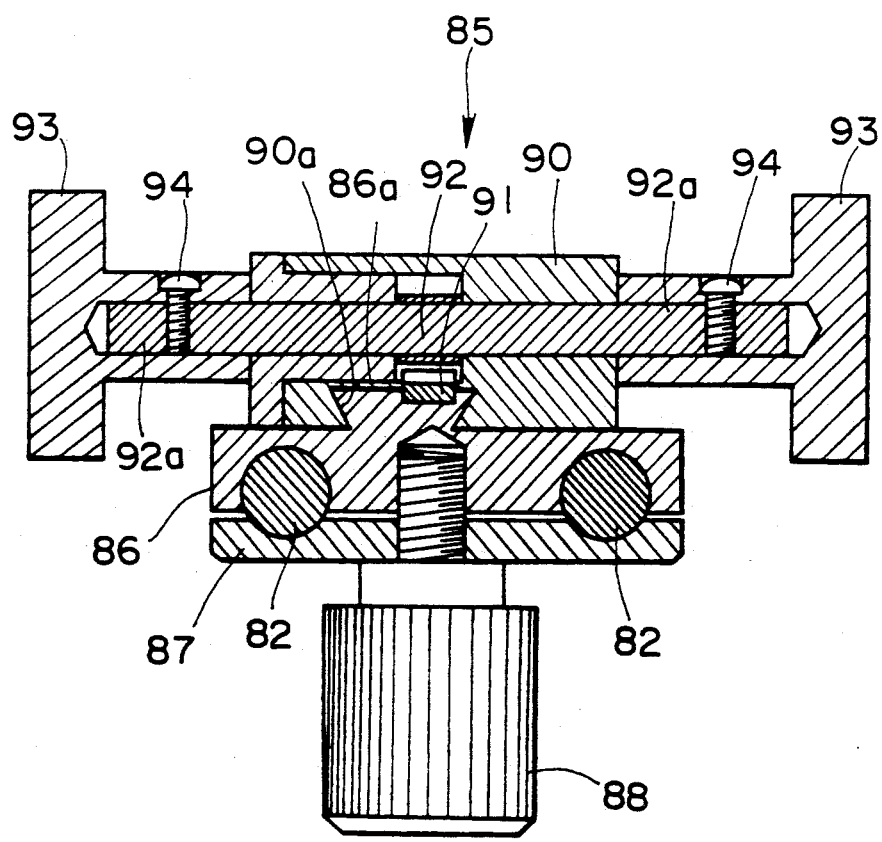
Figure 16:
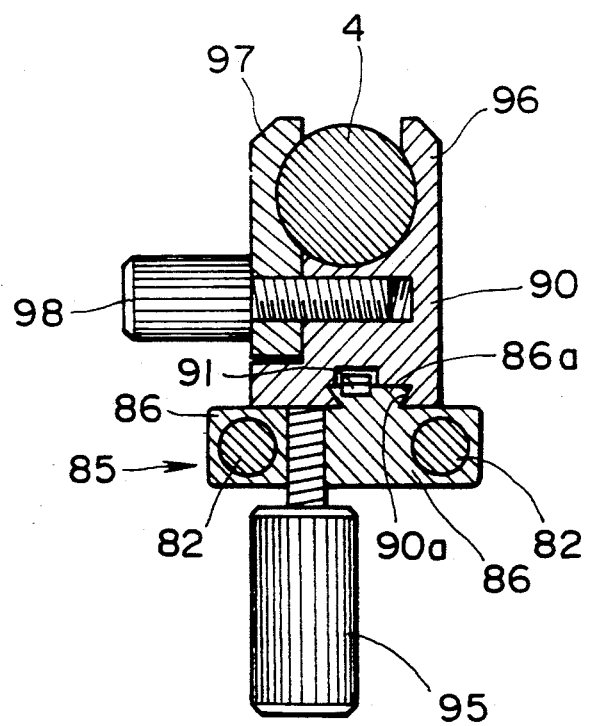

As shown in FIG. 14, the two support shafts 82 secured to the retainer 81 are formed such as to be parallel with the central axis of the sheath-inserting portion 21 and in an elongated manner. A slider 85 is formed midway thereof. This slider 85 has a sliding body 86 in which the two support shafts 82 penetrate the rear-end portion thereof, as shown in FIG. 16, and a lower portion of the front end side thereof is cut out, as shown in FIG. 15. The slider also has a fixing plate 87 which fits with the cut-out portion on the front end side of the sliding body 86. Holes and grooves corresponding to the support shafts 82 are respectively formed in the sliding body 86 and the fixing plate 87, and the arrangement is such that the support shafts 82 are clamped vertically between the sliding body 86 and the fixing plate 87. The slider 85 is secured to the support shafts 82 by means of a pair of setscrews 88 which are screwed into the sliding body 86 by penetrating this fixing plate 87 from the bottom side of the fixing plate 87.

In addition, a supporting body 90 is disposed on the upper side of the sliding body 86. A protrusion 86a and a groove 90a which engage with each other are respectively formed on the upper side of the sliding body 86 and the underside of the supporting body 90 along the axial direction of the sheath 2. The supporting body 90 is slidable relative to the sliding body 86 when this protrusion 86a engages with the groove 90a.

A rack 91 is fixed on the upper surface of the protrusion 86a of the sliding body 86, while a pinion 92 which engages with the rack 91 is provided in the supporting body 90. As shown in FIG. 15, a rotational shaft 92a of the pinion 92 projects from both side portions of the supporting body 90, knobs 93 are respectively fitted to the opposite end portions of the rotational shaft 92a and are secured by screws 94, respectively. When the pinion 92 is rotated by means of the knobs 93, the supporting body 90 can be advanced or retracted relative to the sliding body 86.

As shown in FIG. 2, a reference line 86a is inscribed in the sliding body 86, while a scale 90b is inscribed in the supporting body 90. The arrangement is such that an amount of longitudinal movement of the supporting body 90 in relation to the sliding body 86 can be ascertained from the positions of the reference line 86a and the scale 90b.

As shown in FIG. 16, a setscrew 95 is provided which is screwed into the sliding body 86 in such a manner that a tip thereof is capable of abutting against the supporting body 90 by penetrating the sliding body 86 from the bottom surface of the sliding body 86. When this setscrew 95 is tightened, the supporting body 90 can be secured against the sliding body 86.

The adapter 4 is disposed on an upper portion of the supporting body 90. Specifically, two holding portions 96, which abut against two portions in the front and rear of one side portion of the adapter 4, are respectively provided on the upper surfaces of a front end portion and a rear end portion of the supporting body 90. Two holding plates 97 corresponding to the two holding portions 96 are provided on the other side portion of the adapter 4. A pair of setscrews 98, which respectively penetrate the holding plates 97 and are screwed into the holding portions 86, are provided. The arrangement is such that the adapter 4 is clamped between the holding portions 96 and the holding plates 97 when these setscrews 98 are tightened, thereby allowing the adapter 4 and the holding body to be secured.

Figure 11:
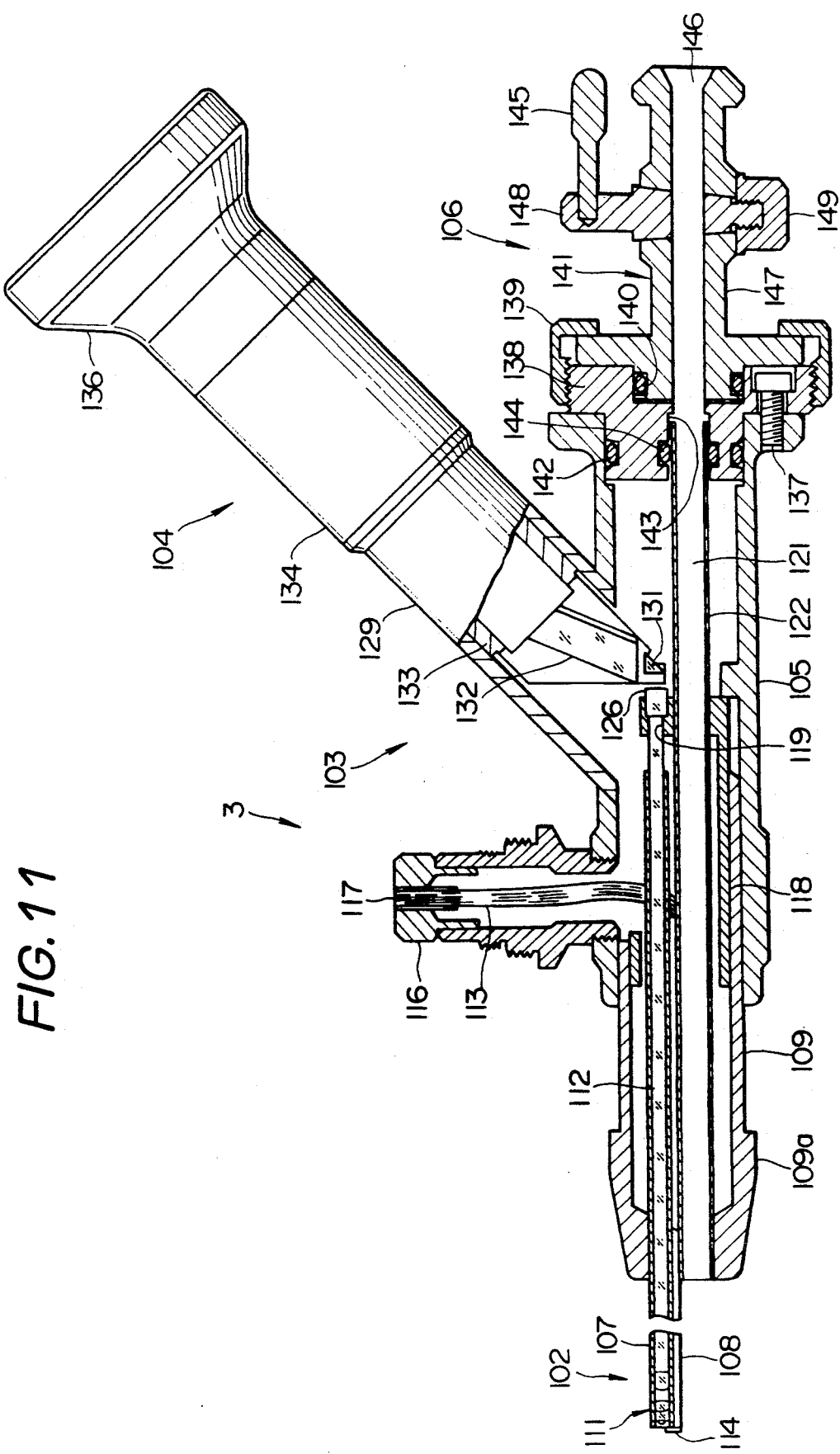
Figure 12:
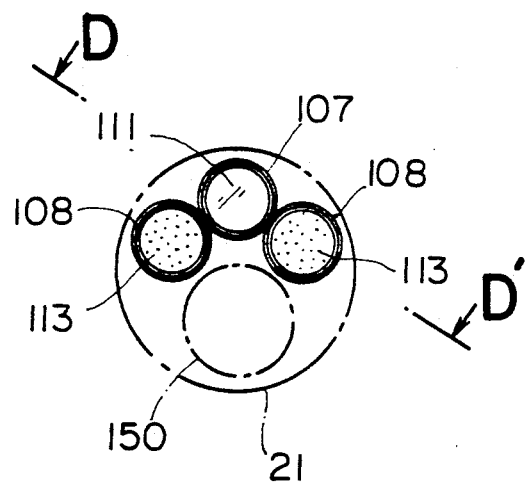
Figure 13:
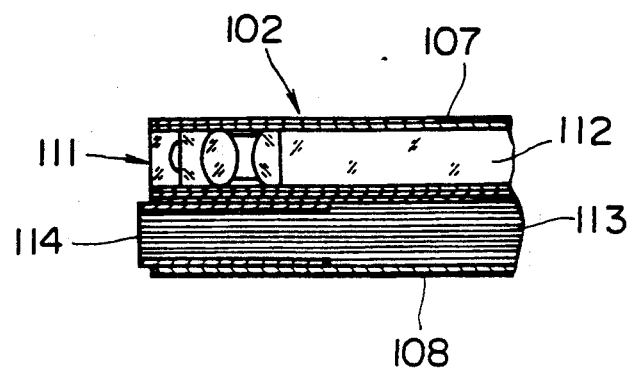

Meanwhile, the telescope 3 which is inserted into the sheath 2 is arranged as shown in FIGS. 11 to 13.

As shown in FIG. 11, the telescope 3 comprises a rigid, elongated inserting section 102, a large-diameter operating section 103 connected to a rear portion of this inserting section 102, an eyepiece section 104 branching diagonally rearwardly from a side portion of the operating section 103, and a treating instrument installing section 106 provided at a rear end portion of the operating section 103. Incidentally, it is also possible to adopt an arrangement (not shown) in which the eyepiece section 104 branches off perpendicularly from a side portion of the operating section 103 and is bent midway thereof rearwardly from the branched-off portion in such a manner that the eyepiece becomes substantially parallel with the operating section 3.

The inserting section 102 has a lens tube 107 and, say, two light guide tubes 108. This lens tube 107 is provided such as to extend through the operating section 103 and is inserted up to the vicinity of a portion thereof from which the eyepiece section 104 extends.

The operating section 103 is provided with a telescope body 105 having the eyepiece section 104 and the treating instrument installing section 106, as well as a connecting member 109 which is provided at a front end portion of the telescope body 105. A connecting portion 109a which is connected to the connecting member 23 of the sheath 2 is provided at a front end portion of this connecting member 109.

As shown in FIGS. 12 and 13, an objective lens system 111 is disposed at a distal end portion of the lens tube 107, while a refractive index-inclining-type lens 112 is disposed in the rear of the objective lens system 111 as an image-transmitting optical system. Light guide fibers 113 are inserted in each of the light guide tubes 108. After the light guide fibers 113 are bonded and secured at the objective-side end portion of each of the light guide tubes 108, front end surfaces 114 thereof are ground and then polished, and the light guide fibers 113 are capable of causing illumination light to be made emergent from these front end surfaces 114. These light guide fibers 113 are inserted into each of the light guide tubes 108, are bent sideways inside the operating section 103, and are bonded to and secured at a light guide connector 116 extending from a side portion of the operating section 103. The rear end surfaces 117 of the light guide fibers 113 are then polished. These end surfaces 117 constitute a plane of incidence of illumination light supplied from the light source device (not shown).

A positioning member 118 is fitted with and secured on a rear end side of the connecting member 109. This positioning member 118 is provided with a fixing hole 119, into which a rear end portion of the refractive index-inclining-type lens 112 exposed such as to project from the lens tube 107 is inserted. Furthermore, a channel tube 122 is provided such as to penetrate the positioning member 118. This channel tube 122 is inserted inside the telescope body 105 from a front end surface of the connecting member 109 in parallel with the lens tube 107, and forms a treating instrument channel 121 which reaches the treating instrument installing section 106.

The eyepiece section 104 is provided with an eyepiece tube 129. Disposed in this eyepiece tube 129 is an eyepiece lens system frame 133 in which a triangular prism 131 and a trapezoidal prism 132 are installed in the rear of the lens 126 so as to refract the optical axis of an observation optical system. An eyepiece outer tube 134 is provided at a rear end of this eyepiece tube 129. Furthermore, an eyepiece 136 is provided at a rear end of the eyepiece outer tube 134.

The treating instrument installing section 106 comprises a closing member 138 which fits with a rear end portion of the telescope body 105 and is fixed by a screw 137, as well as a treating instrument adapter 141 which is detachably installed at a rear end portion of the closing member 138 by means of an attachment ring 139 which is screwed onto said rear end portion.

A fitting outer peripheral surface of the closing member 138 is adapted to maintain airtightness by means of an airtight member 142, such as an O-ring, with respect to the telescope body 105. Furthermore, a hole 143 in which the channel tube 122 fits is formed in a central portion of the closing member 138. An airtight member 144, such as an O-ring, is disposed in this hole 143 so as to maintain airtightness with respect to the channel tube 122.

The treating instrument adapter 141 is fitted with and secured to the closing member 138 in a state in which airtightness is maintained by an airtight member 140, such as an O-ring. The treating instrument adapter 141 is provided with an adapter body 147 having a treating instrument inserting port 146 connunicating with the treating instrument channel 121 at a rear end surface thereof, and is also provided with a cock 148 which is capable of opening and closing the treating instrument inserting port 146. A lever 145 is provided in an upper portion of the cock 148, while a nut 149 is screwed onto a lower portion thereof so as to install the cock 148 on the adapter body 147.

The adapter 4 can be detachably connected to the rear end of the telescope body 105 of the telescope 3 by means of the attachment ring 139 after the treating instrument adapter 141 is removed.

As shown in FIG. 12, in this embodiment, the observation optical system, including the objective lens system 111 and the like, and the light guide fibers 113 are provided separately, and the space other than that for the telescope-inserting portion 102 in the inner hole of the sheath-inserting portion 21 is used as the channel. This arrangement is designed to minimize the outside diameter of the sheath-inserting portion 21 and to minimize the damage to which the patient is is subjected. Depending on cases, the channel tube 122 through which the treating instrument is inserted may be extended over the entire length of the telescope-inserting portion 102.

Incidentally, in FIG. 12, reference numeral 150 denotes a space through which the treating instrument is inserted.

The adapter 4 which is detachably connected to the rear end portion of the telescope body 105 of the telescope 3 as well as the ultrasonic suction device 5 which is inserted into the treating instrument channel of the telescope 3 via the adapter 4 are arranged as shown in FIGS. 17 to 20.

Figure 17:
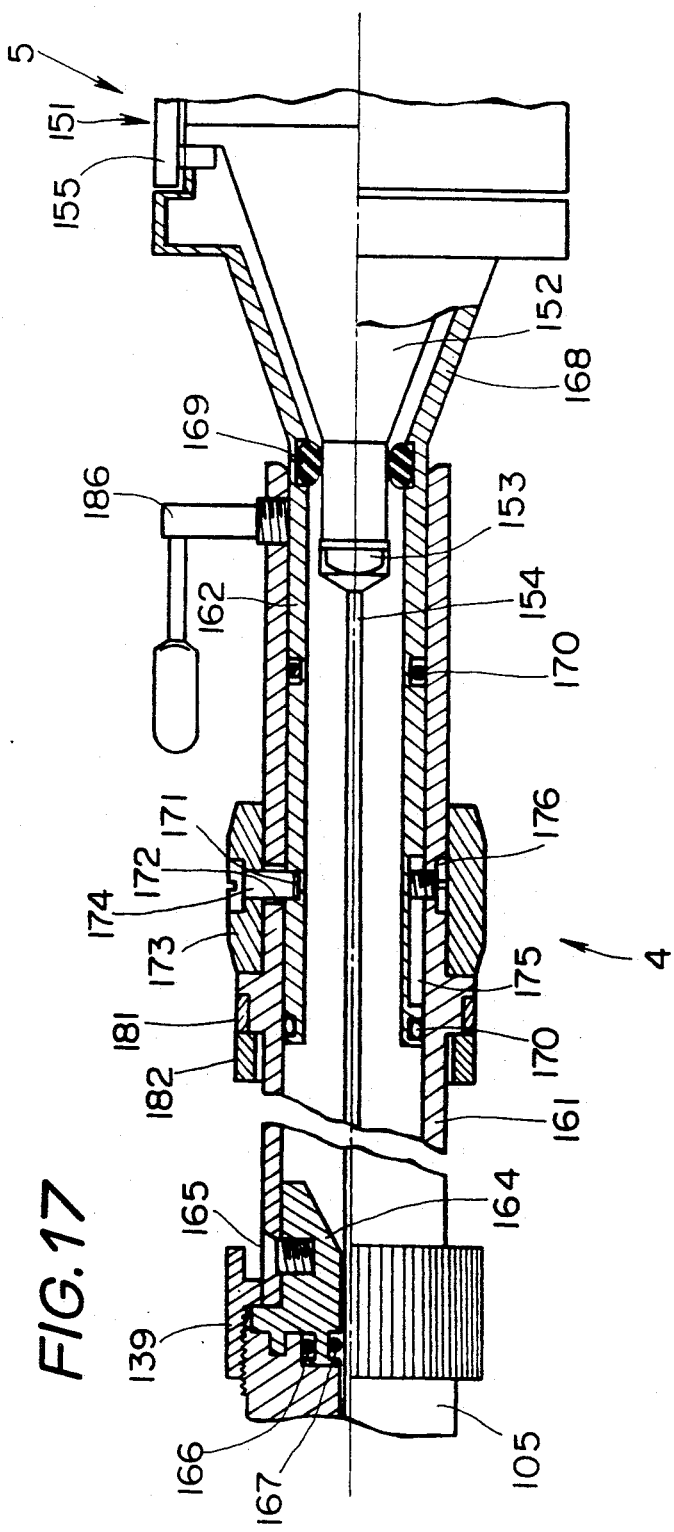

As shown in FIG. 17, the ultrasonic suction device 5 comprises a vibrator section 151 on the operator's side which generates ultrasonic vibrations, as well as an elongated tubular probe 154 connected via a connecting portion 153 to a tip of a horn 152 provided in the vibrator section 151. The inner hole of the probe 154 communicates with the drainage tube 42. An object to be sucked is broken up by ultrasonic vibrations which are generated by the vibrator 151 and are transmitted by the probe 154, and is then sucked by the pump 43 through the inner hole of the probe 154, the drainage tube 42, and the collection bottle 43.

The adapter 4 comprises a substantially cylindrical adapter body 161 and a substantially cylindrical sliding member 162 internally fitted with a rear end portion of the adapter body 161. A connecting member 164, which is detachably connectable to the rear end portion of the telescope body 105 of the telescope 3 by means of the attachment ring 139, is installed at a front end portion of the adapter body 161 by means of a screw 165. The connecting member 164 is provided with 0-rings 166, 167 which are interposed between the connecting member 164 and the telescope body 105. The O-ring 166 is intended to prevent the leakage of a perfusate from inside the adapter 4, while the O-ring 167 is intended to hold a nodal portion of the vibrating probe 154 so as to prevent the probe 154 of the ultrasonic suction device 5 from falling into the brain.

A tapered portion 168 whose greater diameter is at its rear end is formed at a rear end portion of the sliding member 162. The horn 152 of the ultrasonic suction device 5 is accommodated in this tapered portion 168, the rear end portion of which is connected to a cover 155 of the vibrator section 151. An 0-ring 169 is interposed between the sliding portion 162 and the horn 152 so as to prevent the perfusate from flowing into the ultrasonic suction device 5. In addition, a pair of 0-rings 170 for maintaining the liquid-tightness in the adapter 4 are interposed between overlapping portions of the adapter body 161 and the sliding member 162, and these 0-rings serve to prevent the perfusate from flowing to the outside.

A cam groove 171 is provided circumferentially around a peripheral portion of the adapter body 161, and a spiral cam groove 172 communicating with the cam groove 171 is provided around a peripheral portion of the sliding member 162. A cam ring 173 is fitted rotatably around an outer peripheral portion of the adapter body 161, and a cam pin 174 engaging with the cam grooves 171, 172 is secured to this cam ring 173. Furthermore, a straight groove 175 is provided axially on an outer peripheral portion of the sliding member 162. A tip portion of a guide pin 176, which is secured to the adapter body 161 such as to project inwardly, is engaged with the groove 175. The cam pin 174 is adapted to slide along the cam grooves 171, 172 as the cam ring 173 is rotated. Since the circumferential relationship between the adapter body 161 and the sliding member 162 is restricted by the groove 175 and the guide pin 176, the sliding member 162 is adapted to move longitudinally relative to the adapter body 161 as the cam pin 174 moves along the cam groovs 171, 172. In addition, the probe 154 of the ultrasonic suction device 5 moves longitudinally relative to the adapter body 161 in conjunction with the longitudinal movement of the sliding member 162 relative to the adapter body 161.

A scale ring 181 is secured around an outer peripheral portion of the adapter body 161 forwardly of the cam ring 173 by means of a holding ring 182. As shown in FIG. 19, a scale 183 is inscribed on an outer peripheral portion of the scale ring 181, while a reference line 184 is inscribed on an outer peripheral portion the cam ring 183. A distance of longitudinal movement of the cam ring 173 relative to the adapter body 161, i.e., an amount of projection of the tip portion of the probe 154, can be determined from the positions of the scale 183 and the reference line 184.

A setscrew 186, which penetrates the adapter body 161 and whose tip is capable of abutting against an outer peripheral portion of the sliding member 162, is provided on a rear end side of the adapter body 161. The arrangement is such that, when this setscrew 186 is tightened, the tip of the setscrew 186 holds the sliding member 162, thereby making it possible to fix the sliding member 162 at a desired position relative to the adapter body 161, and, at the same time, if the setscrew 186 is loosened, the sliding member 162 can be moved relative to the adapter body 161.

Figure 18:
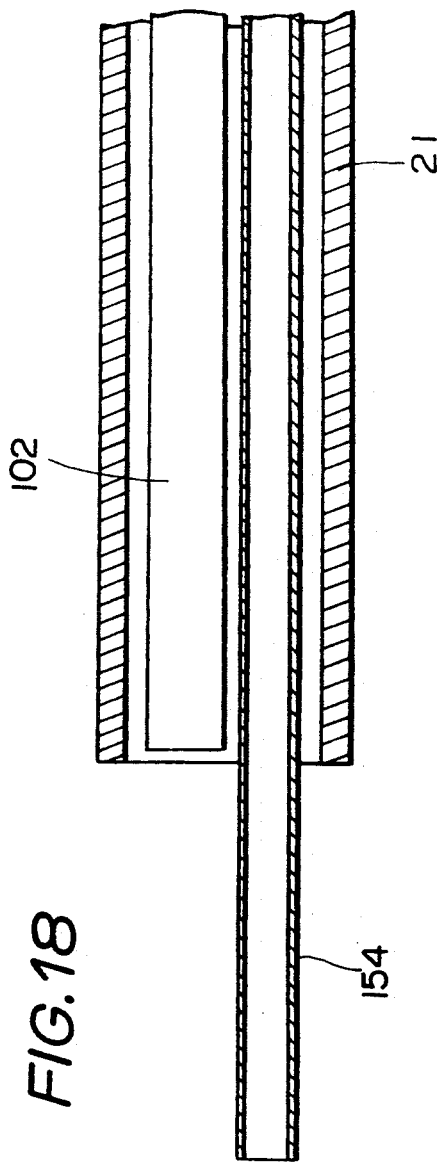

FIGS. 17 and 18 illustrate a state in which the sliding member 162 is disposed at its forward limit. In this state, the tip of the probe 154 of the ultrasonic suction device 4 is adapted to project forwardly of a front end surface of the sheath-inserting portion 21. In addition, FIGS. 19 and 20 illustrate a state in which the sliding member 162 is disposed at its rear limit. In this state, the tip of the probe 154 is flush with the front end surface of the sheath-inserting portion 21, or is slightly retracted therefrom.

A description will now be made of an operation of the cerebral surgery apparatus in accordance with this embodiment having the above-described arrangement.

First, adjustment is made of X, Z, $\theta$, $\gamma$, and $\epsilon$ of the sliding table 53, the support table 55, the rotational cylinder 58, and the arm 63 of the fixing device 6 setting them to the position of the sheath holder 16 determined by the positioner 14, the arm 15, and the sheath holder 16.

Subsequently, the sheath 2 is fixed to the sheath holder 16, and when the setscrew 68 screwed into the rotational member 74 of the sheath holder 16 has entered the groove 67 of the auxiliary arm 66 provided at the distal end portion of the arm 63, the setscrews 54, 56, 59, the shaft 64, the knob 65, and the setscrew 68 are screwed in securely so as to effect fixing.

In addition, the support shaft 82 secured to the retainer 81 of the support 17 is fitted into the support member 73 of the sheath holder 16, which is secured to the arm 15 of the stereotaxic instrument 1 and the arm 63 of the fixing device 6 and to which the sheath 2 is secured in advance. When the retainer 81 has struck against the support member 73, the support member 73 and the retainer 81 of the support 17 are fixed by means of the setscrew 19. The ultrasonic suction device 5 with the probe 154 installed in the horn 152 is secured to the adapter 4 by screwing in or other similar method from the rear end of the sliding member 162 until the cover 155 of the horn 152 abuts against the rear end of the tapered portion 168 of the sliding member 162.

At this time, the adapter 4 is connected to the telescope body 105 by means of the attachment ring 139 via the connecting member 164, with the sliding member 162 of the adapter 4 fully extended relative to the adapter body 161, i.e., in a state in which the sliding member 162 is disposed at its rear limit, as shown in FIGS. 19 and 20.

After the support body 90 of the slider 85 is secured to the adapter 4 which is fixed to the telescope 3 and the ultrasonic suction device 5, the slide body 86 is fitted with the support shafts 82 in such a manner that the inserting portion 102 of the telescope 3 is inserted into the sheath-inserting portion 21. The slider 85, the telescope 3 fixed thereto, the adapter 4, and the ultrasonic suction device 5 are slid in the direction of the supports 82. The telescope 3 and the sheath 2 are secured firmly at a position in which the telescope 3 is completely connected to the sheath 2. Further, the sliding body 86 is securely fixed to the support shafts 82 by means of the setscrews 88. In addition, the support body 90 and the sliding body 86 of the slider 85 are secured by means of the setscrew 95.

In this state, the tip of the probe 154 is flush with or slightly retracted from the tip of the sheath-inserting portion 21. The setscrew 186 is then loosened, and as the cam ring 173 is rotated relative to the adapter body 161, the sliding member 162 is moved forwardly to a desired position relative to the adapter body 161 while the operator is viewing the scale 183. The setscrew 186 is then retightened. In this state, a length of the tip of the probe 154 which is projecting from the end surface of the sheath-inserting portion 21 can be set.

In the cerebral surgery apparatus thus assembled, when the sheath 2, the telescope 3, the adapter 4, and the ultrasonic suction device 5 are integrally moved in the axial direction of the sheath-inserting portion 21, the nut 77 of the sheath holder 16 is loosened to render the sheath-inserting portion 21 to be freely movable relative to the sheath holder 16. In addition, the setscrew 95 of the slider 85 is loosened to make the support body 90 movable relative to the sliding body 86. As the knob 93 of the slider 85 is rotated, the sheath 2, the telescope 3, the adapter 4, the ultrasonic suction device 5, and the support body 90 move integrally in the direction of the central axis of the sheath 2 relative to the sheath holder 17, the support 17, the support shafts 82, the sliding body 86, etc. When the position is determined, the setscrew 95 is tightened to fix these parts.

In addition, when the setscrews 98 of the support body are loosened to loosen the holding plates 97, the sheath 2, telescope 3, adapter 4, and ultrasonic suction device 5 can be rotated integrally.

The ultrasonic suction device 5 breaks up a hematoma 190 such as the one shown in FIG. 3, by means of ultrasonic vibrations transmitted from the horn 152 of the vibrator section 151 to the probe 154, and the broken-up hematoma is sucked by the pump through the inner hole of the probe 154 and is thereby removed. In addition, as a perfusate is supplied through the inner hole of the sheath 2 from the liquid feeding port 25 of the sheath 2, as necessary, the discharged liquid together with the hematoma and the like is sucked and removed through the inner hole of the probe 154. The discharged liquid is collected in the collection bottle 43 via the drainage tube 42, and is then collected in a discharged liquid container (not shown) via the pump 45 and the tube 44.

The procedure of suction, removal, etc. of the hematoma 190 is performed by direct observation using the telescope 3. In this telescope 3, illumination light from the light source device (not shown) is made emergent from the distal end portion of the inserting portion 102 via the light guide 29 connected to the light guide connector 116 of the telescope 3 and the light guide fibers 113 in the telescope 3, and is applied to the part to be observed. A light image returned from this part is formed by the objective lens system 111, and this image is transmitted to the eyepiece section 104 by the observation optical system including the refractive index-inclining-type lens 112 and is observed from the eyepiece 136 of this eyepiece section 104.

Thus, in accordance with the present invention, it is possible to directly observe the state of treatment of an affected portion such as a hamatoma, a cerebral tumor, or the like by means of the telescope 3, and the risk of injuring the undamaged cerebral parenchyma is eliminated, thereby making it possible to perform the procedure very safely and positively.

In addition, the state of the surgical operation can be ascertained on a real-time basis, so that the operating time can be shortened.

Furthermore, since the ultrasonic suction device 5 is used, an affected part, such as a hematoma or a cerebral tumor, can be sucked and removed efficiently with a small-diameter probe. Also, since the small-diameter probe is used, the damage that might otherwise be caused to the cerebral parenchyma as a result of insertion of the suction device can be minimized.

Since the fixing device 6 is provided, there is no need to manually hold and operate the ultrasonic suction device 5, thereby contributing to safety.

Since the fixing device 6 is provided with a mechanism of adjustment in the directions of X, Z, $\theta$, $\gamma$, and $\epsilon$, the position of connecting the sheath holder 16 and the support 17 can be determined accurately.

Furthermore, the weight of the sheath 2, the telescope 3, the adapter 4, and the ultrasonic suction device 5 can be supported while the position thereof determined by the positioner 14, the arm 15, and the sheath holder 16 of the stereotaxic instrument 1 is maintained by the fixing device 6. Accordingly, it is possible to install heavier instruments, including the sheath 2, telescope 3, and treating instrument such as the ultrasonic suction device 5, on the stereotaxic instrument 1, than would otherwise be useable. In addition, since the sheath 2, the telescope 3, and the treating instrument are secured firmly, the surgical operation can be performed more safely and accurately.

Since the fixing device 6 is provided with the slider 85, and as the knob 93 of this slider 85 is rotated, the sheath 2, the telescope 3, the adapter 4, and the ultrasonic suction device 5 can be moved integrally. Consequently, an advancing and retracting operation thereof can be effected accurately and positively, and the surgical operation can be performed safely. Moreover, the efficiency is improved, and the operating time can be shortened. Additionally, since the surgical operation can be performed by fixing the position of the distal end of the ultrasonic suction device 5 at a position where the field of view of the telescope 3 is the easiest to view, there is no need to have the treating instrument project excessively, so that safety is thereby ensured.

An amount of movement of the support body 90 relative to the sliding body 86, i.e., an amount of movement of the sheath 2, the telescope 3, the adapter 4, and the ultrasonic suction device 5 relative to the sheath holder 16 and the support 17 of the fixing device 6, as well as the sliding body 86, and the like, can be ascertained accurately by virtue of the reference line 86 and the scale 90a respectively provided on the sliding body 86 and the support body 90 of the slider 85.

In addition, since the adapter 4 is provided, a length of the probe 154 of the ultrasonic suction device 5 which is projecting from the sheath 2 can be adjusted as desired, so that there is no danger of causing the probe 154 to be projected inadvertently, thereby allowing the surgical operation to be performed safely.

Even if the lengths of the probe 154, the adapter 4, the sheath 2, etc. are varied, by assembling these component parts together prior to the surgical operation, it is possible to effect adjustment of a zero point (a state in which the end surface of the sheath-inserting portion 21 and the end surface of the probe 154 are flush, or the end surface of the probe 154 is slightly retracted therefrom). Therefore, by adjusting the sliding member 162 with the graduation of the zero point as a reference, it is possible to ascertain at hand the projecting length of the probe 154, thereby allowing the surgical operation to be performed safely.

Since the probe 154 does not project even if the operator leaves his hands off the ultrasonic suction device 5, this apparatus is extremely safe.

Since the probe 154 is held resiliently by means of the O-ring 167, should the probe 154 be fractured at a portion thereof welded to the connector 153 or at other similar portion, the probe 154 will not drop into the head, the apparatus is safe.

In addition, since the operator is able to perform treatment within a short period of time while observing through the telescope, the invasion to which the patient is subjected can be minimized, while the fatigue the operator experiences can be alleviated.

Furthermore, since treatment can be conducted positively using the ultrasonic suction device 5, there is no need for the catheter to be retained for a long period of time and for a drug such as a resolvent to be administered, with the result that the occurrence of an infectious disease can be prevented.

Incidentally, since an artifact which causes a CT image to be difficult to view if aluminum, titanium, ceramics, and the like are used, a plastic or the like which does not produce an artifact may be used as the material of the ring 12, arm 15, positioner 14, fixing device 6, sheath holder 16, support 17, sliding device 85, and the like of the stereotaxic instrument 1.

FIG. 21 illustrates a second embodiment of the present invention.

In this embodiment, a support shaft 201 having a rack 202 on an upper surface thereof is provided instead of the support shafts 82 of the support 17 of the fixing device 6 in the first embodiment. Meanwhile, the support body 90 is provided with the pinion 92 engaging with the rack 202, as in the case of the first embodiment. In addition, the adapter 4 to which the telescope 3 and the ultrasonic suction device 5 are connected is secured thereto. As the knob 93 provided on the pinion 92 is rotated, the telescope 3, the adapter 4, the ultrasonic suction device 5, and the sheath 2 together with the support body 90 move integrally on the support shaft 201.

In this embodiment, since a member corresponding to the sliding body 86 in the first embodiment is eliminated, the structure of the slider 85 becomes simple and can be made lightweight.

The other arrangements, operation, and advantages of this embodiment are the same as those of the first emebodiment.

FIG. 22 shows a third embodiment of the present invention.

In this embodiment, in the slider 85, a support body 213 is provided on a support shaft 211 which is provided with a slit 212, or the number of which is increased to two. A support body 213 is provided on this support shaft 211. This support body 213 is arranged such that a setscrew 214 is screwed into the slit 212 or between the two support shafts 211 such as to penetrate the same from the bottom side thereof. In addition, a large-diameter flange 215 formed on a head portion side of this setscrew 214 abuts against the lower side of the support shaft 211, and as the setscrew 214 is tightened, the support shaft 211 is adapted to be clamped by the flange 215 and the support body 213. The telescope 3, the adapter 4, the ultrasonic suction device 5, and the sheath 2 are moved integrally when the setscrew 214 is loosened and the sliding body 213 is slid along the support shaft 211, and these components are secured when the setscrew 214 is retightened.

In accordance with this embodiment, the structure becomes simpler and more lightweight than that in the case of the second embodiment.

The other arrangements, operation, and advantages of this embodiment are the same as those of the first embodiment.

Figure 23:
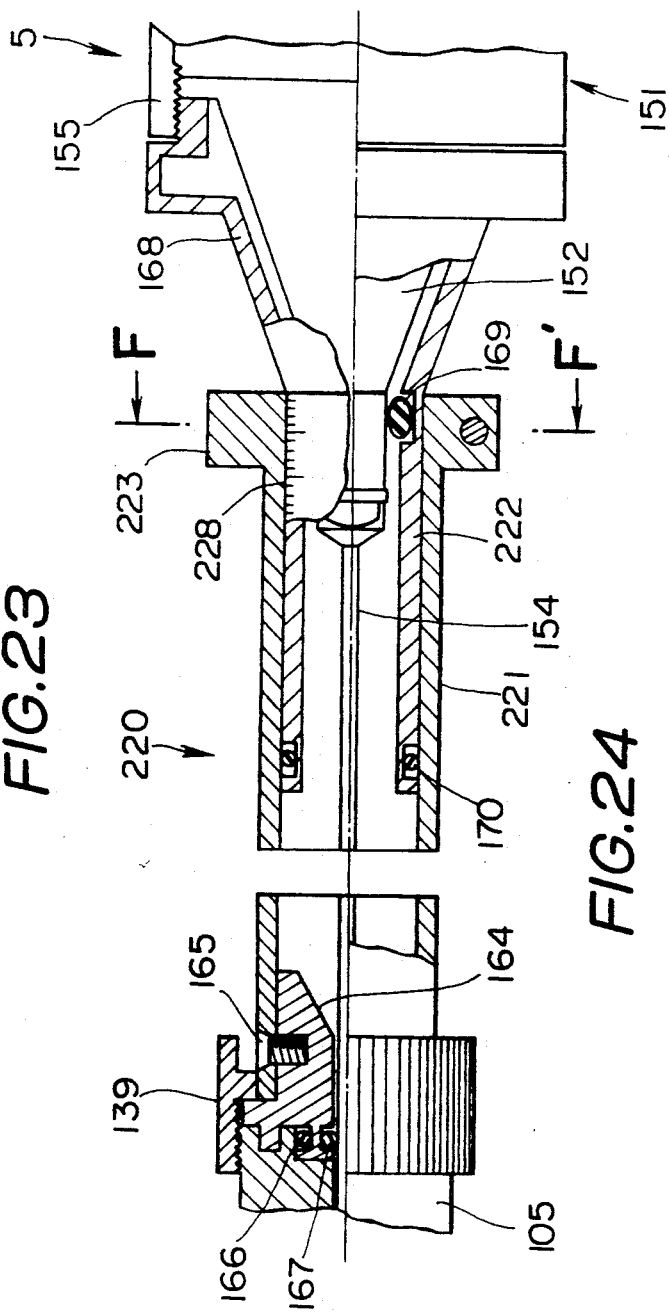
Figure 24:
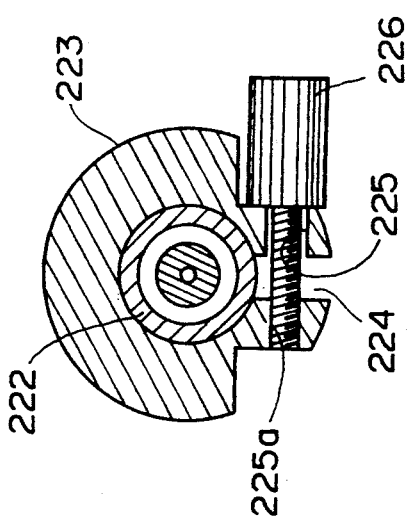

FIGS. 23 and 24 illustrate a fourth embodiment of the present invention.

As shown in FIG. 23, an adapter 220 in this embodiment comprises a substantially cylindrical adapter body 221 and a substantially cylindrical sliding member 222 which is fitted into the inside of the adapter body 221 at a rear end side thereof. A connecting member 164 which is detachably connectable to the rear end portion of the telescope body 105 of the telescope 3 by means of the attachment ring 139 is installed at the front end portion of the adapter body 221, in the same manner as the adapter 4 of the first embodiment.

In addition, the tapered portion 168 is formed at the rear end portion of the sliding member 222, in the same manner as the adapter 4 of the first embodiment.

In this embodiment, a large-diameter flange 223 is formed at the rear end portion of the adapter body 221. As shown in FIG. 24, the flange 223 has a slit 224 formed axially, opposite end portions of this slit 224 being notched such as to be parallel with the end surfaces of the slit 224. In addition, a hole 225 is provided in the flange 223 such as to penetrate the same perpendicular to the slit 224. An internal thread 225a is formed on one side of the slit 224 in the hole 225. A setscrew 226 is inserted into the hole 225 from the side on which the internal thread 225a is not formed, and this setscrew 226 is screwed into the internal thread 225a. As the setscrew 226 is tightened, the interval of the slit 224 is narrowed, thereby securing the sliding member 222 to the adapter body 221. Incidentally, the liquid-tight O-ring 170 is interposed between the adapter body 221 and the sliding member 222.

A scale 228 is inscribed on an outer peripheral surface of the sliding member 222, and this scale 228 makes it possible to confirm the position of the sliding member 222 relative to the adapter body 221.

In this embodiment, the position of the sliding member 222 relative to the adapter body 221 is secured as follows: The setscrew 226 is loosened, and, while confirming the scale 228, the sliding member 222 is adanced or retracted relative to the adapter body 221 in such a manner that the tip of the probe 154 of the ultrasonic suction device 5 projects from the distal end surface of the sheath-inserting portion 21 only by a predetermined length. The setscrew 226 is then retightened.

The other arrangements, operation, and advantages of this embodiment are the same as those of the first embodiment.

Figure 25:
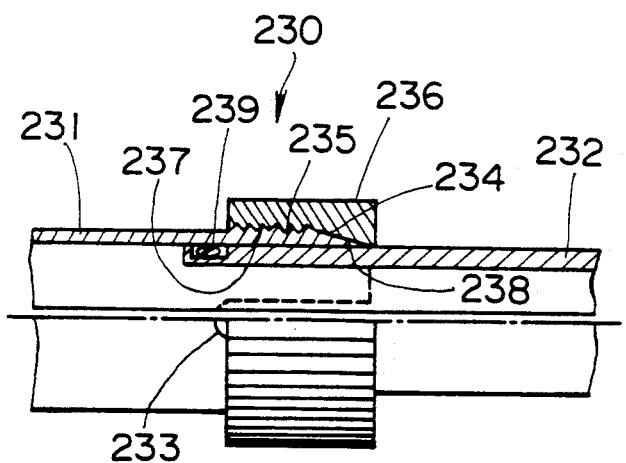
FIG. 25 is a cross-sectional view illustrating a connecting portion for connecting an adapter body and the sliding member of the adapter in accordance with a fifth embodiment of the present invention.

FIG. 25 illustrates a fifth embodiment of the present invention.

An adapter 230 in this embodiment has a plurality of slits 233 formed axially at a rear end portion of an adapter body 231. In addition, a tapered surface 234 having a smaller diameter on a rear end side thereof is formed around an outer peripheral portion of the adapter body 231 at a rear end portion thereof. An external thread 235 if formed around an outer periphery of this tapered surface 234 on an axially forward side thereof. A tightening nut 236 is screwed onto the rear end portion of the adapter body 231. An internal thread 237 which engages with the external thread 235 is formed on an inner periphery of the tightening nut 236 on a front end side thereof, while a tapered surface 238 having a smaller diameter on the rear end side thereof which abuts against the tapered surface 234 is formed on the inner periphery of the tightening nut 236 on the rear end side thereof.

A cylindrical sliding member 232 is fitted in a rear end portion of the adapter body 231 such as to be capable of advancing and retracting, and a liquid-tight 0-ring 239 is interposed between the adapter body 231 and the sliding member 232.

In this embodiment, when the tightening nut 236 is loosened, the sliding member 232 is capable of advancing and retracting relative to the adapter body 231. Meanwhile, if the tightening nut 236 is tightened, the tapered surface 238 at the rear end portion of the tightening nut 236 presses inwardly the tapered surface 234 at the rear end portion of the adapter body 231 and thereby decreases the inside diameter of the rear end portion of the adapter body 231. As a result, the sliding member 232 is secured relative to the adapter body 231.

The other arrangements, operation, and advantages of this embodiment are the same as those of the first embodiment.

Figure 26:
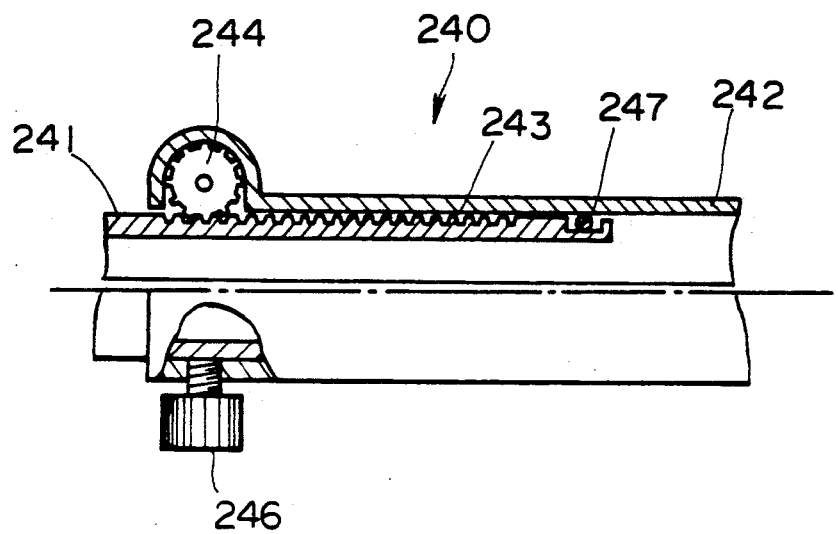
FIG. 26 is a cross-sectional view illustrating a connecting portion for connecting an adapter body and the sliding member of the adapter to the main body of the adapter in accordance with a sixth embodiment of the present invention.

FIG. 26 illustrates a sixth embodiment of the present invention.

In an adapter 240 in this embodiment, a rack 243 is provided along the axial direction on an outer peripheral portion of the adapter body 241. A pinion 244 which meshes with the rack 243 is installed rotatably in a sliding member 242 fitted with the adapter body 241. As a knob (not shown) disposed on an extension of a rotational shaft of the pinion 244 is rotated, the sliding member 242 is adapted to move longitudinally relative to the adapter body 241. In addition, a screw hole which penetrates the sliding member 242 is provided in a side portion of the sliding member 242. The sliding member 242 is adapted to be secured to the adapter body 241 by means of a setscrew 246 screwed in the screw hole. Furthermore, a liquid-tight O-ring 247 is interposed between the adapter body 241 and the sliding member 242.

The other arrangements, operation, and advantages of this embodiment are the same as those of the first embodiment.

Figure 27:
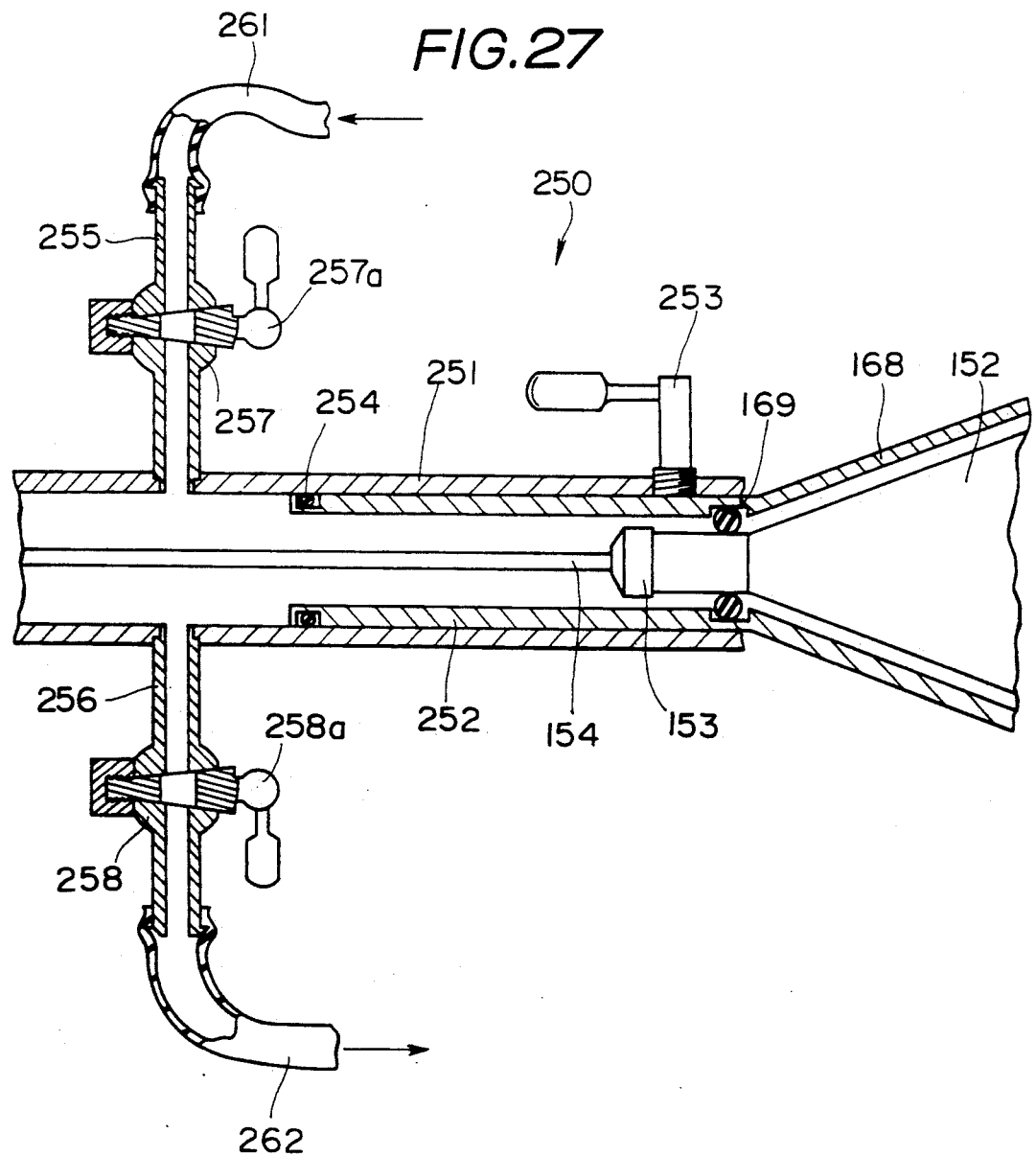
FIG. 27 is a cross-sectional view of the adapter in accordance with a seventh embodiment of the present invention.

FIG. 27 illustrates a seventh embodiment of the present invention.

In an adapter 250 in accordance with this embodiment, a sliding member 252 is fitted in a rear end portion of an adapter body 251 such as to be capable of advancing and retracting. This sliding member 252 is adapted to be secured when a setscrew 253 screwed into the adapter body 252 in a penetrating manner is tightened. A liquid-tight 0-ring 254 is interposed between the adapter body 251 and the sliding member 252.

In this embodiment, a refrigerant inlet 255 and a refrigerant outlet 256 which communicate with the inside of the adapter body 251 are provided in an outer peripheral portion of the adapter body 251. The refrigerant inlet 255 and the refrigerant outlet 256 are respectively provided with cocks 257, 258. The arrangement is such that when cock levers 257a, 258a of the cocks 257, 258 are operated, an amount of the refrigerant flowing in and flowing out can be controlled. In addition, a liquid feeding tube 261 and a liquid discharging tube 262 are respectively connected to the refrigerant inlet 255 and the refrigerant outlet 256.

In this embodiment, a refrigerant is allowed to flow from the refrigerant inlet 255 into the adapter body 251, and this refrigerant is discharged from the refrigerant outlet 256. The probe 154 of the ultrasonic suction device 5 can be cooled by this refrigerant. As a result, it is possible to check the generation of heat resulting from ultrasonic vibration of the probe 154, thereby allowing any fracture of the probe 154 to be prevented.

The other arrangements, operation, and advantages of this embodiment are the same as those of the first embodiment.

Figure 28:
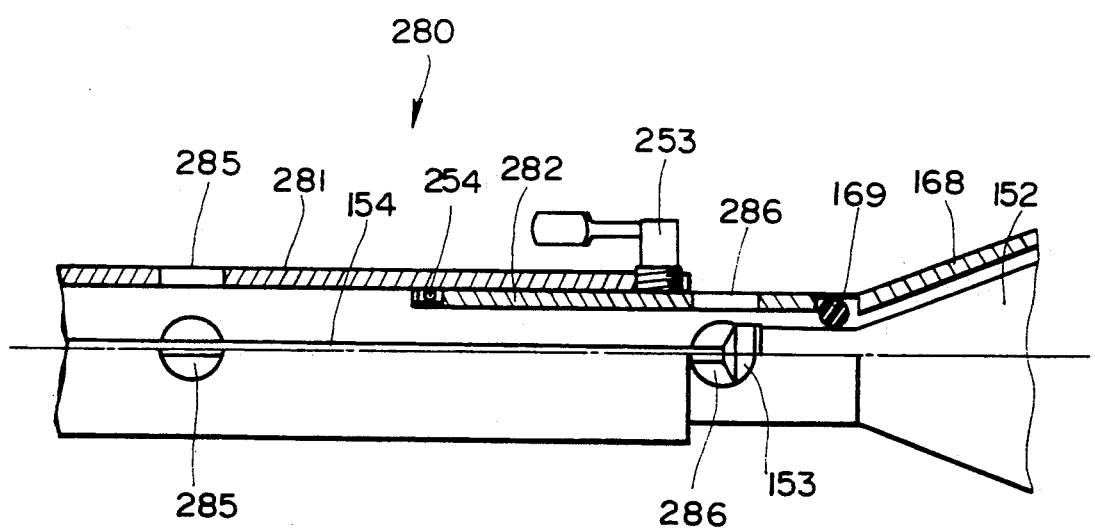
FIG. 28 is a cross-sectional view of the adapter in accordance with an eighth embodiment of the present invention.

FIG. 28 illustrates an eighth embodiment of the present invention.

In an adapter 280 in accordance with this embodiment, a sliding member 282 is fitted in a rear end portion of an adapter body 281, in the same way as the seventh embodiment. The arrangement is such that the sliding member 282 can be secured as a setscrew 253 screwed into the adapter body 281 in a penetrating manner is tightened. A liquid-tight 0-ring 254 is interposed between the adapter body 281 and the sliding member 282.

In this embodiment, a window 285 which makes it possible to confirm a probe 254 therethrough is provided in the adapter body 281, and a window 286 which makes it possible to confirm the connecting portion 153 and the probe 254 is provided in the sliding member 282.

In this embodiment, the state of the probe 254 inside the adapter 280 can be confirmed readily through the windows 285, 286, so that even if any abnormality, such as a crack or breakage, has occurred, the abnormality can be confirmed. Consequently, it is possible to prevent the probe 254 from dropping into the head, so that the apparatus is safe.

The other arrangements, operation, and advantages of this embodiment are the same as those of the first embodiment.

Figure 29:
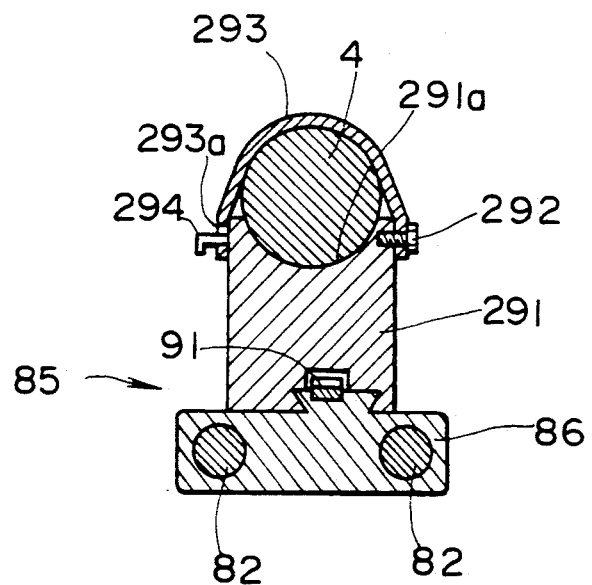
FIG. 29 is a cross-sectional view illustrating an adapter-fixing portion of the support in accordance with a ninth embodiment of the present invention.

FIG. 29 illustrates a ninth embodiment of the present invention.

In this embodiment, a holding belt 293 having one side thereof secured to a support body 291 by means a setscrew 292 is provided on the upper side of one side portion of the support body 291 of the slider 85. A hole 293a is provided in an open end of this holding belt 293, and is adapted to be engaged with a pin 294 provided on an upper side of the other side portion of the support body 292 so as to be secured. A recess 291a into which the adapter 4 is engaged is formed on an upper surface of the support body 291. The adapter 4 is wrapped with the holding belt 291 for a half of its circumference, and the adapter 4 is adapted to be secured to the support body 292 when the pin 294 is engaged into the hole 293a of the holding belt 293.

The other arrangements, operation, and advantages of this embodiment are the same as those of the first embodiment.

Figure 30:
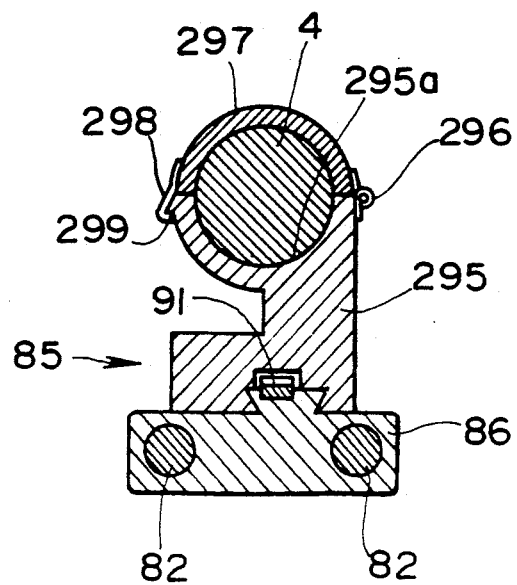
FIG. 30 is a cross-sectional view illustrating the adapter-fixing portion of the support in accordance with a tenth embodiment of the present invention.

FIG. 30 illstrates a tenth embodiment of the present invention.

In this embodiment, a holding arm 297 having one side thereof secured to a support body 295 by a hinge 296 is provided on an upper side of one side portion of the support body 295 of the slider 85. A fixing claw 298 is provided at an open end of this holding arm 297 and is adapted to be fixed by being engaged with a projection 299 formed on an upper side of the other side portion of the support body 295. In addition, a recess 295a into which the adapter 4 is engaged is formed on an upper surface of the support body 295. The arrangement is such that the adapter 4 is clamped between the support body 295 and the holding arm 297, and the fixing claw 298 of the holding arm 297 is engaged with the projection 299, thereby allowing the adapter 4 to be fixed to the support body 295. Incidentally, if the inner surface of the arm 297 is made coarse, a frictional force increases and fixing thereof can be effected more positively.

The other arrangements, operation, and advantages of this embodiment are the same as those of the first embodiment.

Incidentally, although in the first to tenth embodiments the adapter 4 is adapted to be secured to the support body of the slider 85, the slider 85 may be secured to at least one of the adapter 4, the telescope 3, the sheath 2, and the ultrasonic suction device 5.

Figure 31:
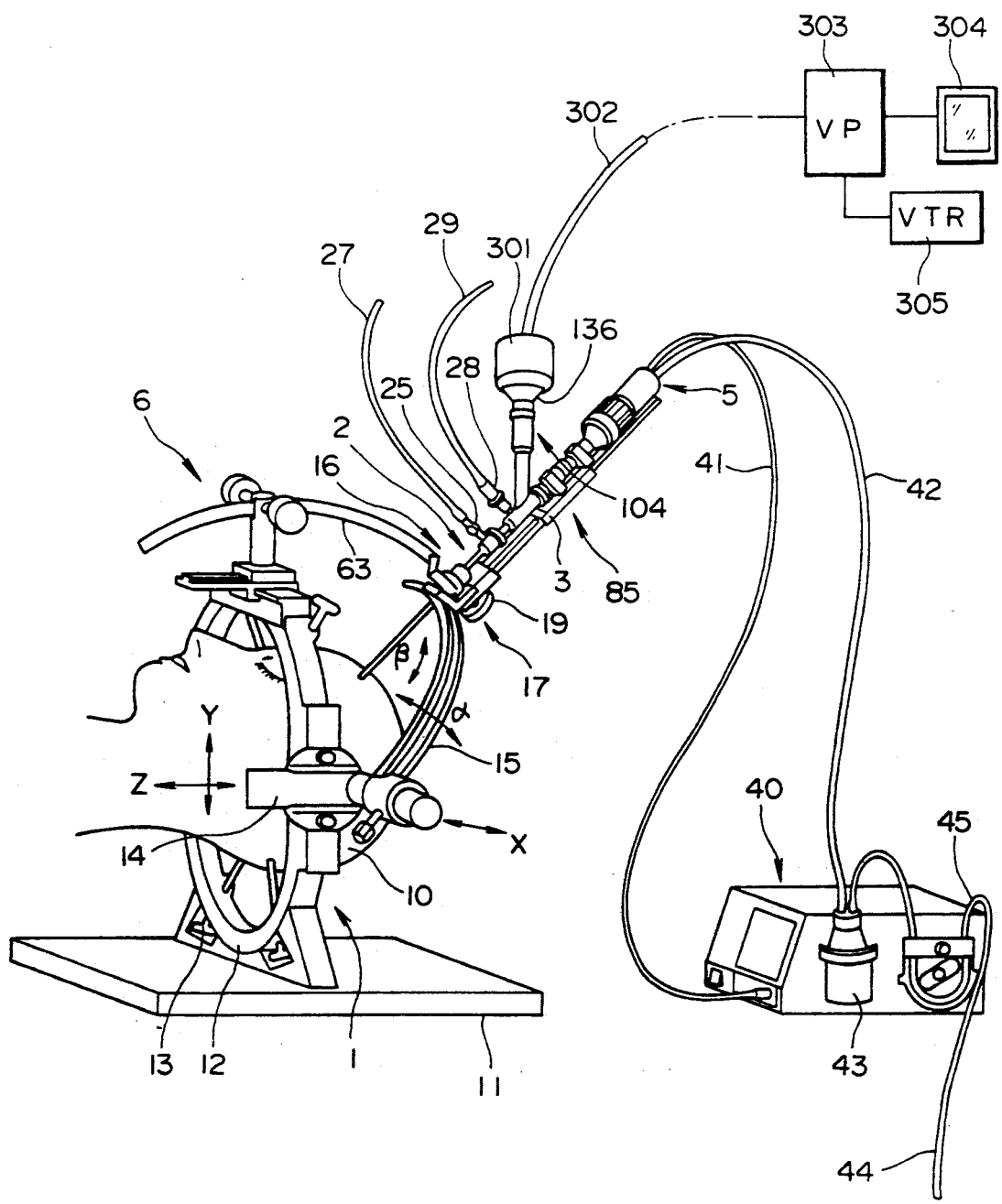
FIG. 31 is a perspective view illustrating the overall cerebral surgery apparatus in accordance with an eleventh embodiment of the present invention.

FIG. 31 illustrates an eleventh embodiment of the present invention.

In this embodiment, a detachable television camera 301 is connected to the eyepiece 136 of the eyepiece section 104 of the telescope 3. This television camera 301 has an image-forming lens (not shown) for forming a light image from the eyepiece section 104 and a solid-state image sensor, such as a CCD (charge-coupled image sensor), disposed at an image-forming position of this image-forming lens. An electric cord 302 connected to the solid-state image sensor is adapted to be connected to a video processor (VP) 303 for processing signals for the television camera 301. This video processor 303 has, for instance, a driver for driving the solid-state image sensor of the television camera 301 as well as a video signal processing circuit for generating video signals from signals output from the solid-state image sensor that have been read out from this driver. The video signals generated in the video signal processing circuit are adapted to be input to a monitor 304. An observation image is displayed on this monitor 304. A video tape recorder (VTR) 305 is connected to the video processor 303, and the observation image shot by the television camera 301 is adapted to be recorded by the video tape recorder 305.

In this embodiment, an image observed through the telescope 3 is shot by the television camera 301, signals output from the television camera 301 are subjected to video signal processing by the video processor 303, and an observation image is displayed on the monitor 304.

According to this embodiment, since the operator is able to perform a surgical operation while observing the image displayed on the monitor 304, he is able to perform the operation in a comfortable posture. In addition, an amount of fatigue he experiences with respect to his eyes is small, which contributes to preventing an erroneous judgment from being made. Furthermore, since a large number of people can observe the image at one time, this arrangement makes it possible to make an objective judgment, and education can thereby be conducted effectively.

If the television camera 301 is connected to the telescope 3, as in the case of this embodiment, the weight of the overall system becomes heavier, so that it would otherwise become extremely difficult for the operator to hold the system with his hands. Hence, the fixing device 6 proves effective.

Incidentally, an arrangement may also be provided such that a viewfinder is provided to the television camera 301 so as to allow the operator to view through the viewfinder and observe the image.

The other arrangements, operation, and advantages of the present invention are the same as those of the first embodiment.

Figure 32:
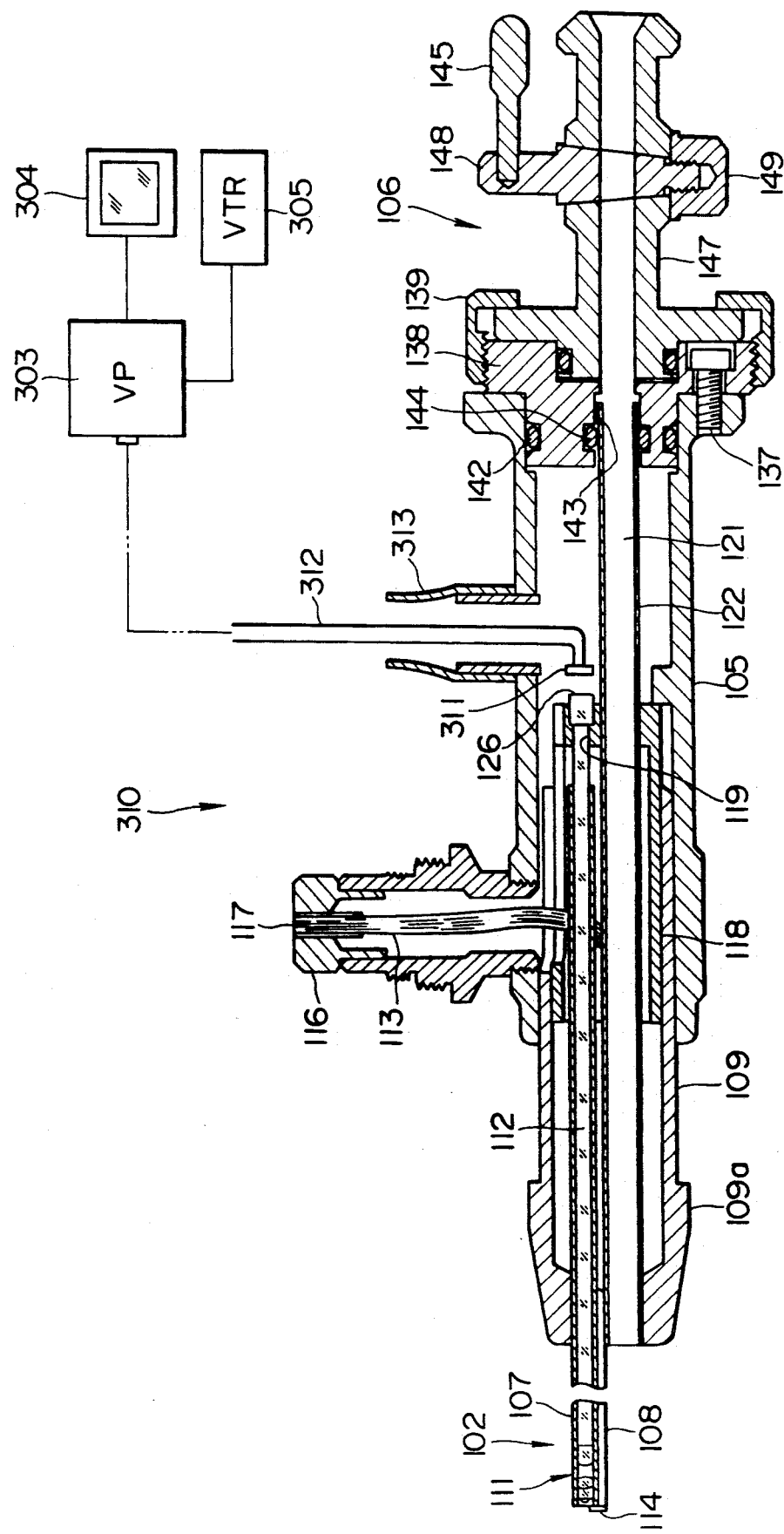
FIG. 32 is a cross-sectional view illustrating the telescope in accordance with a twelfth embodiment of the present invention.

FIG. 32 illustrates a twelfth embodiment of the present invention.

A telescope 310 in accordance with this embodiment has a solid-state image sensor 311 at an image-forming position of the lens 126 disposed at a rear end of the refractive index-inclining-type lens 112. In addition, a cord 313 extends from a side portion of the telescope body 105, and a connector which is detachably connectable to the video processor 303 is disposed at a distal end of the cord 313. A signal line 312 is connected to the solid-state image sensor 311, and this signal line 312 is inserted into the cord 313 and is adapted to be connected to the video processor 303 via the connector. The monitor 304 and the video tape recorder 305 are connected to the video processor 303 as in the case of the eleventh embodiment.

In this embodiment, an observation image formed by the objective lens system 111 and transmitted by the refractive index-inclining-type lens 112 is formed on the solid-state image sensor 311 by the lens 126, and is picked up by the solid-state image sensor 311. This observation image is then displayed on the monitor 304.

According to this embodiment, the telescope 310 and the like can be made more lightweight than in the case where the television camera 301 is connected to the eyepiece 136 of the telescope 3 as in the case of the eleventh embodiment. Hence, this arrangement contributes to making the overall system lightweight.

Incidentally, the position of the solid-state image sensor 311 is not restricted to the illustrated example, and it may be located at the image-forming position of the objective lens 111, or, in a case where not the refractive index-inclining-type lens 112 but a relay lens system is used as an image-transmitting optical system, either of image-forming positions on the inner and outer sides of this relay lens system may be used.

In addition, an arrangement may be provided such that, by providing a prism or other similar beam splitter between the lens 126 and the solid-state image sensor 311, one beam obtained by splitting by this beam splitter is made incident upon the viewfinder, and the other beam is made incident upon the solid-state image sensor 311, thereby making it possible to observe the image through the viewfinder and on the monitor 304 simultaneously.

The other arrangements, operation, and advantages of this embodiment are the same as those of the eleventh embodiment.

Figure 33:
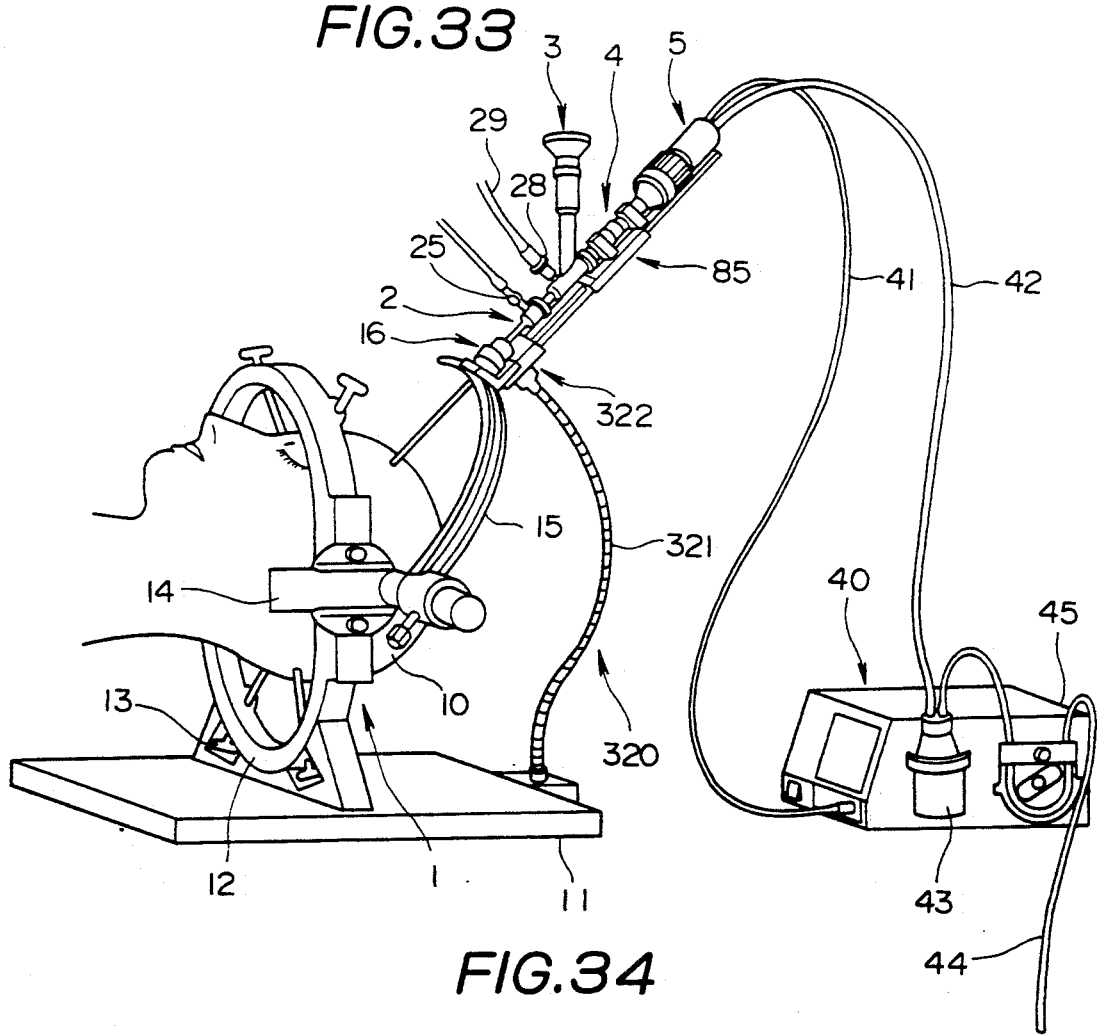
Figure 34:
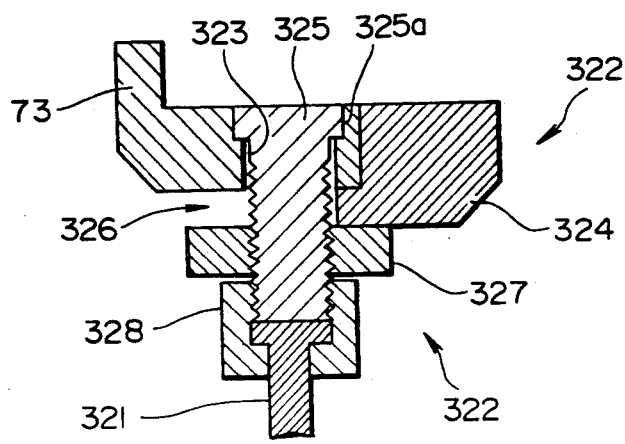

FIGS. 33 and 34 illustrate a thirteenth embodiment of the present invention.

As shown in FIG. 33, a fixing device 320 in accordance with this embodiment has a flexible tube 321 which is secured to, for example, the operating table 11 and has rigidity sufficient to withstand the weight of the sheath 2, the telescope 3, the adapter 4, and the ultrasonic suction device 5 with the tube 321 bent and its shape fixed, as well as a support 322 disposed at a distal end of the tube 321.

As shown in FIG. 34, the support 322 has a support body 324 which is secured to the support member 73 of the sheath holder 16 in the same way as the first embodiment. A hole 323 with which a head 325a of a support screw 325 is capable engaging is formed in the support member 73. The support screw 325 is inserted in this hole 323 such as to project downwardly. Meanwhile, a groove 326 into which the support screw can be inserted is formed in the support body 324. A setscrew 327 is screwed into the support screw 325 from a bottom side of the support body 324 with the support screw 325 inserted into the groove 326. As the setscrew 327 is tightened, the support member 73 and the support body 327 are clamped by the head 325a of the support screw 325 and the setscrew 327, thereby securing the support screw 325, the support member 73, the support body 324, and the setscrew 327.

Meanwhile, the distal end portion of the tube 321 is provided with an enlarged diameter and is accommodated in a tube-fixing nut 328. This tube-fixing nut 328 is screwed onto the support screw 325 projecting downwardly from a bottom portion of the setscrew 327, and the tube 321 is adapted to be secured to the support scew 325 by means of the tube-fixing nut 328.

In this embodiment, since the tube 321 can be deformed as desired, the support 322 is arranged at a position determined by the positioner 14, the arm 15, and the sheath holder 16 of the stereotaxic instrument 1.

According to this embodiment, the structure of the fixing device 320 can be made simple, the operation is facilitated, and the costs of the apparatus can be reduced.

Incidentally, the tube 321 may be fixed at, for instance, the top portion of the ring 12 of the stereotaxic instrument 1.

The other arrangments, operation, and advantages of this embodiment are the same as those of the first embodiment.

Figure 35:
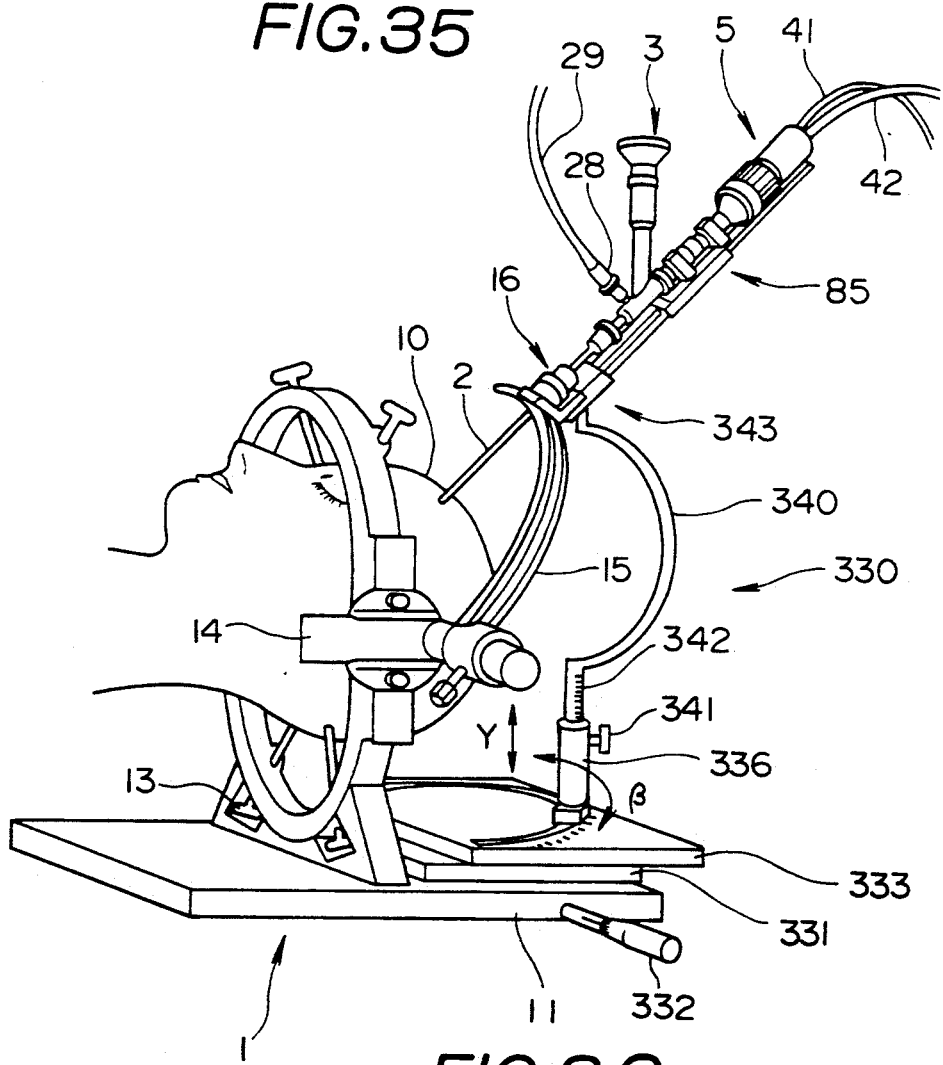
FIGS. 35 and 36 relate to a fourteenth embodiment of the present invention.
Figure 36:
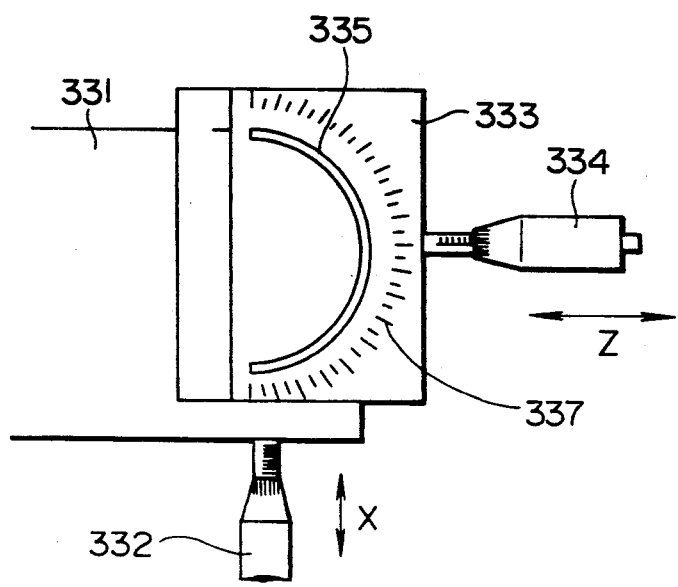

FIGS. 35 and 36 illustrate a fourteenth embodiment of the present invention.

In a fixing device 330 in accordance with this embodiment, a first stage 331 is mounted on the operating table 11. The position of this stage 331 in the direction of X is adjustable by means of an adjusting knob 332. A second stage 333 is mounted on the first stage 331, and the position of this second stage 333 in the direction of Z is adjustable by means of an adjusting knob 334. A semicircular groove 335 is formed on an upper surface of the second stage 333, and a support tube 336 is fitted in this groove 335. The support tube 336 is capable of moving along the groove 335, and the position of the support tube 336 in the direction of $\beta$ is adjustable by being set to a semicircular scale 337 disposed on the outer or inner side of the groove 335. An arm 340 is fitted in the support tube 336 from above. A lower side of this arm 340 is formed straight such as to allow an amount of insertion into the support tube 336 to be varied. In addition, a scale 342 is provided around an outer periphery of the portion of the arm 340 which is inserted into the support tube 336. Furthermore, the arrangement is such that a setscrew 341 is screwed into a side portion of the support tube 336, and after the position of the arm 340 in the direction of Y has been adjusted to the scale 342, the arm 340 is adapted to be secured to the support tube 336 by means of the setscrew 341. The arm 340 is formed such as to be bent so that it will not come into contact with the head 10 of the patient, and a support 343 for integrally supporting the sheath 2, the telescope 3, the adapter 4, and the ultrasonic suction device 5 is secured on an upper portion of the arm 340. Incidentally, a connecting portion for connecting the arm 340 and the support 343 is arranged such that its connecting angle and a connecting direction can be varied freely and fixed.

According to this embodiment, since a mechanism for adjusting the X, Z, $\beta$, and Y directions is provided in the fixing device 330, it is possible to effect accurate adjustment of the position of the support 343.

In addition, since support is provided from below, even if the weight of the sheath 2, the telescope 3, the adapter 4, and the ultrasonic suction device 5 becomes heavy, these components can be supported stably.

The other arrangements, operation, and advantages of this embodiment are the same as those of the first embodiment.

Figure 37:
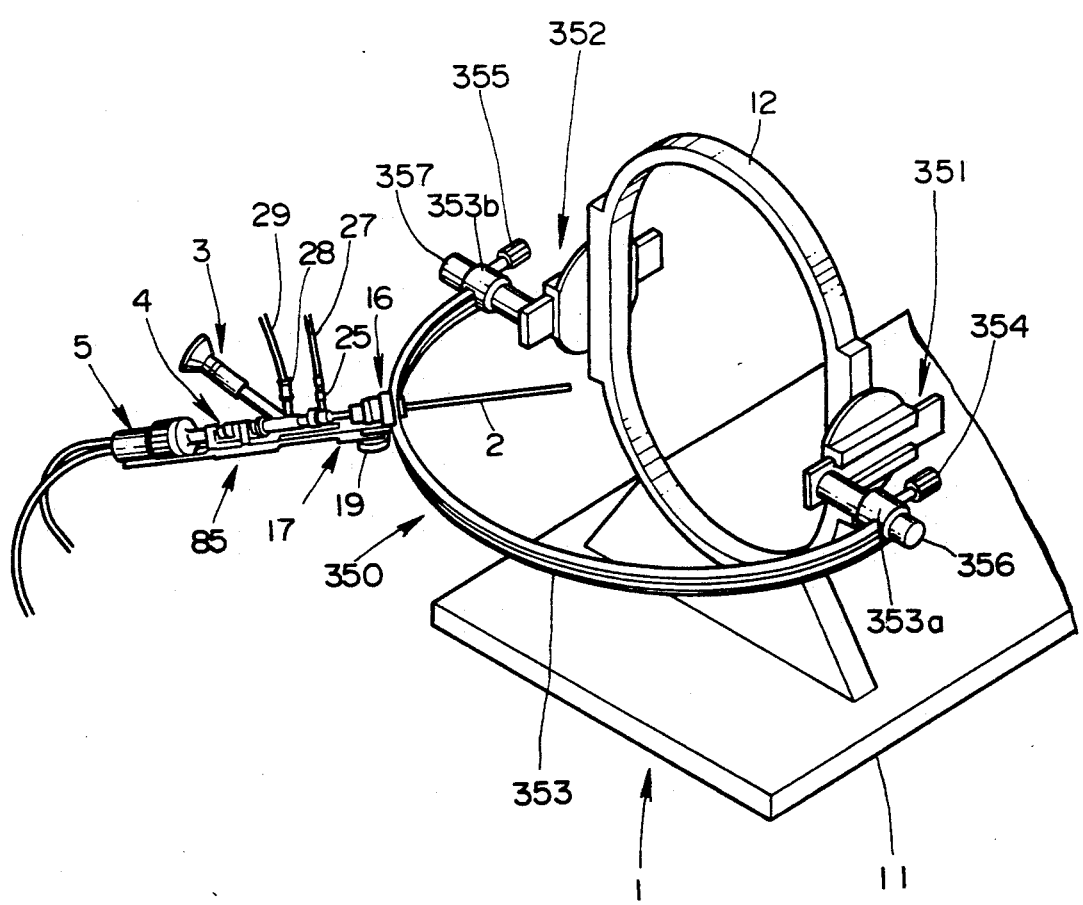
FIG. 37 is a perspective view illustrating the overall cerebral surgery apparatus in accordance with a fifteenth embodiment of the present invention.

FIG. 37 illustrates a fifteenth embodiment of the present invention.

In a fixing device 350 in accordance with this embodiment, positioners 351, 352 that are similar to that of the first embodiment are provided on both sides of the ring 12 of the stereotaxic instrument 1. Annular portions 353a, 353b respectively provided at end portions of an arm 353 are fitted around columns 356, 357 of the positioners 351, 352, and are adapted to be secured by setscrews 354, 355 screwed thereinto from outer peripheral sides of the annular portions 353a, 353b after positioning is effected.

Incidentally, a plastic or the like which does not produce an artifact may be used as the material of the ring 12, arm 353, fixing device 350, positioners 351, 352, setscrews 354, 355, etc. of the stereotaxic instrument 1.

The other arrangements, operation, and advantages of this embodiment are the same as those of the first embodiment.

FIGS. 38 to 41 illustrate a sixteenth embodiment of the present invention.

In a fixing device 360 in accordance with this embodiment, as shown in FIG. 38, positioners 361, 362 that are similar to the positioner 14 of the first embodiment are provided on both sides of the ring 12 of the stereotaxic instrument 1, in the same way as the fifteenth embodiment. Annular portions 363a, 363b provided at end portions of an arm 363 are fitted around columns 366, 367 of the positioners 361, 362, and are adpated to be secured by setscrews 364, 365 screwed therein from outer peripheral sides of the annular portions 363a, 363b after positioning is effected.

An arrangement may alternatively be provided as shown in FIG. 39 so as to secure the arm 363 more positively. In other words, a tightening portion 371 having a tapered surface 371a whose smaller diameter is at its end and which is formed around its outer peripheral surface and having a plurality of slits 371b is provided on the annular portion 363a (363b) of the arm 363. Meanwhile, an external thread 372 is formed on the column 366 (367). A nut 373 which engages with the external thread 372 and has a tapered surface 373a abutting against the tapered surface 371a of the tightening portion 371 is screwed onto the column 366 (367). As this nut 373 is tightened, the tapered surface 373a of the nut 373 presses the tapered surface 371a of the tightening portion 371 to reduce the diameter of the tightening portion 371, thereby positively securing the annular portion 363a (363b) and the column 366 (367).

In addition, an arrangement may alternatively be provided as shown in FIG. 40. In other words, an external thread 381 is provided on the column 366 (367), and two nuts 383, 384 are screwed around the external thread 381 by clamping the annular portion 363a (363b)

of the arm 363. The annular portion 363a (363b) is clamped by the nuts 383, 384, and the annular portion 363a (363b) and the column 366 (367) are thereby secured.

Incidentally, the ring 12, the positioners 361, 362, the setscrews 364, 365, etc. of the stereotaxic instrument 1 may be formed of a plastic or the like so as to prevent the occurrence of an artifact, in the same way as the fifteenth embodiment.

Figure 41:
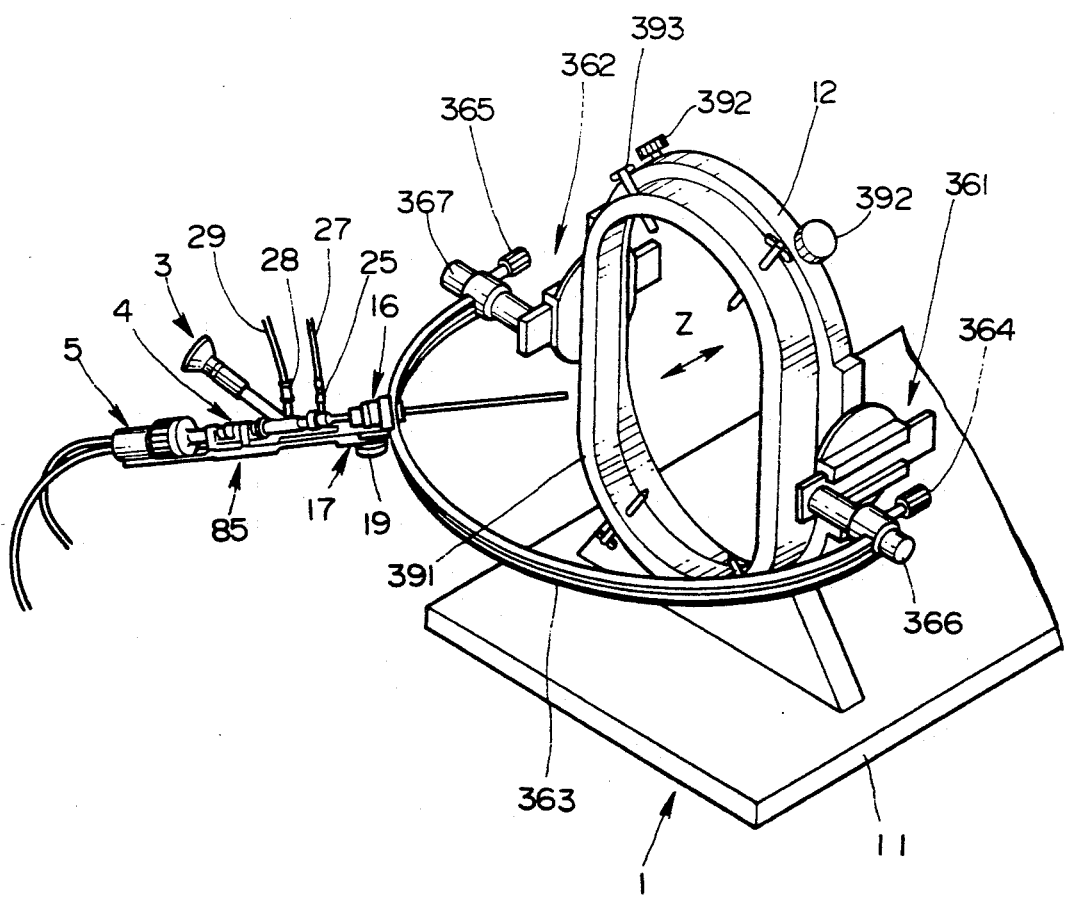

In addition, as shown in FIG. 41, an arrangement may be provided such that an inner ring 391 with a larger width in the Z direction than that of the ring 12 is provided on the inner side of the ring 12 of the stereotaxic instrument 1, and this inner ring 391 is secured by setscrews 392 provided on the ring 12. A plurality of setscrews 393 are provided in the inner ring 391, and the head of the patient is secured by these setscrews 393. In a surgical operation, when the head of the patient is to be moved in the Z direction relative to the stereotaxic instrument 1, the setscrews 392 are first loosened, and the inner ring 391 is then moved relative to the ring 12. Subsequently, the setscrews 392 are retightened, thereby fixing the inner ring 391 relative to the ring 12. Incidentally, the inner ring 391 may also be formed of a plastic so as not to produce an artifact.

According to this embodiment, the sheath 2, the telescope 3, the adapter 4, and the ultrasonic suction device 5 are positioned by the arm 363 of the stereotaxic instrument 1, and their weight is supported thereby. Hence, the structure of the cerebral surgery apparatus can be made simple.

In addition, since the supporting of the weight is effected together with positioning, operations of adjustment and fixing can be faciliated.

Furthermore, since parts of the stereotaxic instrument 1 are formed of a plastic or the like, the occurrence of an artifact affecting a CT image can be prevented.

Moreover, since the inner ring 391 which is slidable relative to the ring 12 is provided, and the head of the patient is secured to this inner ring 391, it becomes possible to move the patient relative to the stereotaxic instrument 1 during a surgical operation, thereby facilitating the surgical operation.

The other arrangements, operation, and advantages of this embodiment are the same as those of the first embodiment.

Incidentally, the present invention is not restricted to the foregoing embodiments, and a treating instrument is not restricted to the ultrasonic suction device 5, but a high-frequency electrode, a laser probe, forceps, a syringe, or the like may be employed.

As has been described above, in accordance with the present invention, since treatment can be performed while directly observing by the telescope the state of treatment of an affected part such as a hematoma, a tumor, or the like on a real-time basis, treatment can be performed safely, positively, and within a short period of time.

In the present invention, it will be obvious to those skilled in the art that various modifications and variations are possible without departing from the scope and spirit of the invention which is solely defined in its claims.

What is claimed is:

1. A cerebral surgery endoscope apparatus comprising:
   a stereotaxic instrument to be secured to the head of a patient to effect positioning of a treating instrument in an affected part;
   treating instrument inserting means whose inserting direction is determined by said stereotaxic instrument, for inserting treating instruments into the head of the patient, a rear end of said inserting means extending to and operatively connecting with said stereotaxic instrument, and an overall length of said inserting means being hollow; and
   a telescope detachably inserted into said inserting means having a channel into which a treating instrument can be inserted and further having an insertable part to be inserted into said inserting means,
   said telescope and channel being removably inserted into said inserting means in a state that the longitudinal axis of the insertable part of said telescope and the longitudinal axis of said inserting means are substantially in parallel, and said treating instrument being removably insertable into said channel, and further
   said telescope and channel being removably insertable into said inserting means allowing supplying or draining of liquid through a cavity of said inserting means while said telescope is removably inserted into said inserting means.

2. A cerebral surgery endoscope apparatus comprising:
   a stereotaxic instrument to be secured to the head of a patient to effect positioning of a treating instrument in an affected part;
   treating instrument inserting means whose inserting direction is determined by said stereotaxic instrument, for inserting treating instruments into the head of the patient;
   a telescope detachably inserted into said inserting means having a channel into which a treating instrument can be inserted and further having an insertable part to be inserted into said inserting means,
   said telescope and channel being removably inserted into said inserting means in a state that the longitudinal axis of the insertable part of said telescope and the longitudinal axis of said inserting means are substantially in parallel, and said treating instrument being removably insertable into said channel, and further
   said telescope and channel being removably insertable into said inserting means allowing supplying or draining of liquid through a cavity of said inserting means while said telescope is removably inserted into said inserting means; and
   a fixing device connected to said stereotaxic instrument to support and fix said inserting means and said telescope with respect to said stereotaxic instrument, a rear end of said inserting means extending to and operatively connecting with said fixing device, and an overall length of said inserting means being hollow.

3. A cerebral surgery endoscope apparatus comprising:
   a stereotaxic instrument to be secured to the head of a patient to effect position of a treating instrument in an affected part;
   an inserting means whose inserting direction is determined by said stereotaxic instrument, for inserting treating instruments into the head of the patient, a rear end of said inserting means extending to and operatively connecting with said stereotaxic instrument, and an overall length of said inserting means being hollow; and a telescope detachably inserted into said inserting means having a channel into which a treating instrument can be inserted and further having an insertable part to be inserted into said inserting means, said telescope and channel being removably inserted into said inserting means in a state that the longitudinal axis of the insertable part of said telescope and the longitudinal axis of said inserting means are substantially in parallel, and said telescope and channel being removably insertable into said inserting means allowing supplying or draining of liquid through a cavity of said inserting means while said telescope is removably inserted in said inserting means, and further said treating instrument being removably insertable into said channel, said treating instrument being insertable into said channel of said telescope and then into the head of the patient.

4. A cerebral surgery endoscope apparatus according to claim 3, further comprising:

an adapter for detachably connecting said treating instrument and said telescope.

5. A cerebral surgery endoscope apparatus according to claim 4, wherein said treating instrument is an ultrasonic suction instrument having a tubular probe, and said adapter includes a hollow portion into which said probe is inserted and an inlet and an outlet for a refrigerant for cooling said probe inserted into said hollow portion.

6. A cerebral surgery endoscope apparatus according to claim 4, wherein said treating instrument is an ultrasonic suction instrument having a tubular probe, and said adapter includes a cylindrical member into which said probe is inserted and a window allowing presence of said probe inserted in said cylindrical member to be confirmed.

7. A cerebral surgery endoscope apparatus according to claim 4: wherein said treating instrument is removably insertable into said channel of said telescope and then into the head of the patient wherein said adapter includes a telescope-side connecting portion detachably connectable to said telescope, a treating instrument-side connecting portion detachably connectable to said treating instrument, connecting means for connecting said telescope side connecting portion and said treating instrument-side connecting portion such as to allow the same to advance and retract, and fixing means which is capable of fixing positions of said telescope-side connecting portion and said treating instrument-side connecting portion at desired positions, a rear end of said inserting means extending to and operatively connecting with said adapter, and an overall length of said inserting means being hollow.

8. A cerebral surgery endoscope apparatus according to claim 7, further comprising a fixing device connected to said stereotaxic instrument and adapted to support and fix said inserting means, said telescope, said adapter, and said treating instrument.

9. A cerebral surgery endoscope apparatus according to claim 7 or 8, wherein said adapter includes at a front end portion thereof a substantially tubular adapter body having said telescope-side connecting portion and at a rear end portion thereof said treating instrument-side connecting portion, said adapter further including a sliding member fitted slidably at a rear end portion of said adapter body; a moving device having a cam ring fitted rotatably around the outer peripheral portions of said adapter body and said sliding member, cam grooves provided in said adapter body and said sliding member, and a cam pin which is secured to said cam ring, is engaged into said cam grooves, and is slidable along said cam grooves so as to make said sliding member longitudinally movable relative to said adapter body by the rotation of said cam ring; a scale indicating the position of said sliding member relative to said adapter body; and a setscrew capable of fixing said sliding member to said adapter body.

10. A cerebral surgery endoscope apparatus according to claim 7 or 8, wherein said adapter includes at a front end portion thereof a substantially tubular adapter body having said telescope-side connecting portion and at a rear end portion thereof said treating instrument-side connecting portion, said adapter further including a sliding member fitted slidably at a rear end portion of said adapter body, a scale for indicating the position of said sliding member relative to said adapter body, and a fixing member which is capable of fixing said sliding member to said adapter body when the outside diameter of outer periphery-side members of said adapter body and said sliding member is reduced.

11. A cerebral surgery endoscope apparatus according to claim 7 or 8, wherein said adapter includes at a front end portion thereof a substantially tubular adapter body having said telescope-side connecting portion and at a rear end portion thereof said treating instrument-side connecting portion, said adapter further including a sliding member fitted slidably at a rear end portion of said adapter body, a moving device having a rack provided on one of said adapter body and said sliding member and a pinion provided on the other and engaging with said rack, thereby making it possible to move said sliding member longitudinally relative to said adapter body as said pinion is rotated, and a setscrew capable of fixing said sliding member to said adapter body.

12. A cerebral surgery endoscope apparatus comprising:

a stereotaxic instrument to be secured to the head of a patient to effect positioning of a treating instrument in an affected part;

an inserting means whose inserting direction is determined by said stereotaxic instrument and which is inserted into the head of the patient;

a telescope detachably inserted into said inserting means having a channel into which a treating instrument can be inserted and further having an insertable part to be inserted into said inserting means;

said telescope and channel being removably inserted into said inserting means in a state that the longitudinal axis of the insertable part of said telescope and the longitudinal axis of said insert means are substantially in parallel, and said telescope and channel being removably insertable into said inserting means allowing supplying or draining of liquid through a cavity of said inserting means while said telescope is removably inserted in said inserting means, and further said treating instrument being removably insertable into said channel, said treating instrument being inserted into said channel of said telescope and then into the head of the patient; and a fixing device connected to said stereotaxic instrument to support and secure said inserting means, said telescope, and said treating instrument, a rear end of said inserting means extending to and operatively connecting with said fixing device, and an overall length of said inserting means being hollow.

13. A cerebral surgery endoscope apparatus according to claim 12, wherein said inserting means can insert treating instruments into the head of the patient; wherein said treating instrument is removably insertable into said channel of said telescope and then into the head of the patient; and wherein said apparatus further comprises:

an adapter for detachably connecting said treating instrument and said telescope.

14. A cerebral surgery endoscope apparatus according to any one of claims 1 to 13, wherein said telescope includes an elongated inserting portion which is adapted to be inserted into said inserting means, illumination means for making illumination light emergent from a distal end portion of said inserting portion; an image-forming optical system provided at said distal end portion of said inserting portion, an eyepiece section provided at a rear end portion of said inserting portion, and an image-transmitting optical system for transmitting an image formed by said image-forming optical system to said eyepiece section.

15. A cerebral surgery endoscope apparatus according to any one of claims 1 to 13, wherein said telescope includes a telescope body and a treating instrument installing section which is detachable from said telescope body.

16. A cerebral surgery endoscope apparatus according to claim 14, further comprising a television camera connected detachably to said eyepiece section and display means for displaying an image picked up by said television camera.

17. A cerebral surgery endoscope apparatus according to any one of claims 1 to 13, wherein said telescope includes an elongated inserting portion which is inserted into said inserting means, illumination means for making illumination light emergent from a distal end portion of said inserting portion, an image-forming optical system provided at a distal end portion of said inserting portion, and image pickup means using a solid-state image sensor for sensing an image formed by said image-forming optical system.

18. A cerebral surgery endoscope apparatus according to any one of claims 3 to 13, wherein said treating instrument is an ultrasonic suction instrument.

19. A cerebral surgery endoscope apparatus according to claim 18, wherein said ultrasonic suction instrument includes a vibrator section for generating ultrasonic vibrations, a tubular probe connected to said vibrator section and adapted to transmit the ultrasonic vibrations, and suction means for sucking an object to be sucked through a hollow portion of said probe.

20. A cerebral surgery endoscope apparatus according to any one of claims 1 to 13, wherein said stereotaxic instrument has an inner ring for fixing the head of a patient and an outer ring for fixing said inner ring such as to adjust the position of said inner ring.

21. A cerebral surgery endoscope apparatus comprising:

a stereotaxic instrument to be secured to the head of a patient to effect positioning of a treating instrument in an affected part;

an inserting means whose inserting direction is determined by said stereotaxic instrument, for inserting treating instruments into the head of the patient;

a telescope detachably inserted into said inserting means having a channel into which a treating instrument can be inserted and further having an insertable part to be inserted into said inserting means;

said telescope and channel being removably inserted into said inserting means in a state that the longitudinal axis of the insertable part of said telescope and the longitudinal axis of said inserting means are substantially in parallel, and said telescope and channel being removably insertable into said inserting means allowing supplying or draining of liquid through a cavity of said inserting means while said telescope is removably inserted in said inserting means, and further said treating instrument being removably insertable into said channel, said treating instrument being insertable into said channel of said telescope and then into the head of the patient; and a fixing device connected to said stereotaxic instrument to support and fix said inserting means, said telescope, and said treating instrument, said fixing device having moving means which is capable of allowing said inserting means, said telescope, and said treating instrument to be advanced and retracted in an inserting direction of said inserting means, a rear end of said inserting means extending to and operatively connecting with said fixing device, and an overall length of said inserting means being hollow.

22. A cerebral surgery endoscope apparatus according to claim 21, wherein said fixing device has means which allows said inserting means, said telescope, and said treating instrument to be rotated.

23. A cerebral surgery endoscope apparatus according to claim 21, further comprising an adapter for detachably connecting said treating instrument and said telescope.

24. A cerebral surgery endoscope apparatus according to claim 23, wherein said fixing device has a support for supporting said sheath, said telescope, and said treating instrument, and said moving means is fixed to at least one of said inserting means, said telescope, said treating instrument, and said adapter and has a slider which is longitudinally slidable relative to said support.

25. A cerebral surgery endoscope apparatus according to claim 24, wherein said slider includes a guide portion connected to said support, a sliding body which is longitudinally slidable along said guide portion, a support member which is secured to at least one of said inserting means, said telescope, said treating instrument, and said adapter and is longitudinally slidable relative to said sliding body, fixing means for fixing said sliding body relative to said guide portion, and fixing means for fixing said support member relative to said sliding body.

26. A cerebral surgery endoscope apparatus according to claim 25, wherein said slider includes a moving device having a rack which is provided one of either said sliding body and said support member and a pinion provided on the other and meshing with said rack, thereby allowing said support member to be longitudinally movable relative to said sliding body as said pinion is rotated.

27. A cerebral surgery endoscope apparatus according to claim 26, wherein a scale indicating the position of said support member relative to said sliding body is provided on one of said sliding body and said support member.

28. A cerebral surgery endoscope apparatus according to claim 26, wherein said support member has a clamping portion for clamping and fixing said adapter.

29. A cerebral surgery endoscope apparatus according to claim 26, wherein said support member has a belt wound around an outer peripheral portion of said adapter and adapted to fix said support member and said adapter.

30. A cerebral surgery endoscope apparatus according to claim 26, wherein said support member has an arm for fixing said support member and said adapter by pressing an outer peripheral portion of said adapter.

31. A cerebral surgery endoscope apparatus according to claim 24, wherein said slider has a guide portion and support member which is secured to at least one of said inserting means, said telescope, said treating instrument, and said adapter and is longitudinally movable along said guide portion.

32. A cerebral surgery endoscope apparatus according to claim 31, wherein said slider further has a rack provided on either one of said guide portion and said support member and a pinion provided on the other and meshing with said rack, thereby allowing said support member to be longitudinally movable relative to said guide portion as said pinion is rotated.

33. A cerebral surgery endoscope apparatus comprising:
   a stereotaxic instrument to be secured to the head of a patient to effect positioning of a treating instrument in an affected part;
   an inserting means whose inserting direction is determined by said stereotaxic instrument, for inserted treating instruments into the head of the patient;
   a telescope detachably inserted into said inserting means having a channel into which a treating instrument can be inserted and further having an insertable part to be inserted into said inserting means;
   said telescope and channel being removably inserted into said inserting means in a state that the longitudinal axis of the insertable part of said telescope and the longitudinal axis of said inserting means are substantially in parallel, and
   said telescope and channel being removably insertable into said inserting means allowing supplying or draining of liquid through a cavity of said inserting means while said telescope is removably inserted in said inserting means, and further
   said treating instrument being removably insertable into said channel,
   said treating instrument being insertable into said channel of said telescope and then into the head of the patient; and
   a fixing device connected to said stereotaxic instrument to support and fix said treating instrument, said fixing device having adjusting means allowing the position of said treating instrument to be adjusted, a rear end of said inserting means extending to and operatively connecting with said fixing device, and an overall length of said inserting means being hollow.

34. A cerebral surgery endoscope apparatus according to claim 33, further comprising an adapter for detachably connecting said treating instrument and said telescope.

35. A cerebral surgery endoscope apparatus according to claim 33 or 34, wherein said fixing device has a position adjusting mechanism fixed to said stereotaxic instrument, an arm connected to said position adjusting mechanism, and an inserting means holder provided at an end portion of said arm and adapted to hold said inserting means.

36. A cerebral surgery endoscope apparatus according to claim 33 or 34, wherein said fixing device has a support member which is fixed to said stereotaxic instrument and is flexible but rigid enough to support said inserting means, said telescope, and said treating instrument, as well as an inserting means holder connected to said support member and adapted to hold said inserting means.

37. A cerebral surgery endoscope apparatus according to claim 33 or 34, wherein said fixing device has a position adjusting mechanism fixed to said stereotaxic instrument, an inserting means holder for holding said inserting means, and an arm connecting said position adjusting mechanism and said inserting means holder and adapted to support said inserting means holder from below.

38. A cerebral surgery endoscope apparatus according to claim 33 or 34, wherein said fixing device has a position adjusting mechanism fixed to said stereotaxic instrument, an arm opposite end portions of which are respectively connected to said position adjusting mechanism, and an inserting means holder fixed at a desired position on said arm and adapted to hold said inserting means.

39. A cerebral surgery endoscope apparatus according to claim 33 or 34, wherein said stereotaxic instrument and said fixing device are made of material, such as a plastics, which does not produce an artifact for a CT image.

40. A cerebral surgery endoscope apparatus according to claim 12, further comprising:
   an adapter for detachably connecting a telescope and said treating instrument inserted into said treating instrument channel to said telescope, said adapter comprising:
   a telescope-side connecting portion detachably connectable to said telescope;
   a treating instrument-side connecting portion detachably connectable to said treating instrument;
   connecting means for connecting said telescope-side connecting portion and said treating instrument-side connecting portion such as to be capable of advancing and retracting the same; and
   fixing means capable of fixing the positions of said telescope-side connecting portion and said treating instrument-side connecting portion at desired positions.

41. A cerebral surgery endoscope apparatus according to claim 4
   wherein said adapter detachably connects said treating instrument and said telescope, said adapter including a telescope-side connecting portion detachably connectable to said telescope, a treating instrument-side connecting portion detachable connectable to said treating instrument, connecting means for connecting said telescope-side connecting portion such as to allow the same to advance and retract, and fixing means which is capable of fixing position of said telescope-side connecting portion and said treating instrument-side connecting portion at desired positions.

42. A cerebral surgery endoscope apparatus comprising:
   a stereotaxic instrument to be secured to the head of a patient, including a support means and means for positionally orienting the support means with respect to an affected part;
   treating instrument inserting means supported on the support means for receiving a treating instrument to be inserted into the affected part for treatment thereof, a rear end of said inserting means extending to and operatively connecting with the support means, and an overall length of said inserting means being hollow; and
   a viewing instrument supported on the support means and operatively associated with said treating instrument inserting means so as to be insertable therewith into the affected part to provide real time observation of the treatment, and further having an insertable part to be inserted into said inserting means,
   said viewing instrument being removably inserted into said treating instrument inserting means in a state such that the longitudinal axis of the insertable part of said viewing instrument and the longitudinal axis of said inserting means are substantially in parallel, and said treating instrument being removably insertable in said inserting in said inserting means with said viewing instrument, and further
   said said viewing instrument and treating instrument being removably insertable into said inserting means allowing supplying or draining of liquid through a cavity of said inserting means while said viewing instrument is removably inserted in said inserting means.

43. Endoscope apparatus as recited in claim 42 wherein said viewing instrument is an endoscope.

44. An endoscope apparatus as recited in claim 43 wherein said endoscope includes illumination means, an image forming optical system, and a solid-state image sensing means.

45. An endoscope apparatus as recited in claim 42 further including fixing means for securing the stereotaxic instrument, support means, treating instrument inserting means, and viewing instrument in fixed position with respect to said affected part.

* * * * *